US011369895B2

(12) United States Patent
Ciftci

(10) Patent No.: US 11,369,895 B2
(45) Date of Patent: Jun. 28, 2022

(54) NANOPOROUS STARCH AEROGELS IMPREGNATED WITH PHYTOSTEROLS AND METHODS OF PREPARING THE NANOPOROUS STARCH AEROGELS

(71) Applicant: NUtech Ventures, Lincoln, NE (US)

(72) Inventor: Ozan Nazim Ciftci, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 41 days.

(21) Appl. No.: 15/875,720

(22) Filed: Jan. 19, 2018

(65) Prior Publication Data

US 2018/0207546 A1 Jul. 26, 2018

Related U.S. Application Data

(60) Provisional application No. 62/448,544, filed on Jan. 20, 2017.

(51) Int. Cl.

| | |
|---|---|
| *A23L 29/212* | (2016.01) |
| *A23L 33/11* | (2016.01) |
| *A23L 33/125* | (2016.01) |
| *A23P 10/00* | (2016.01) |
| *A61K 47/38* | (2006.01) |
| *A61K 9/51* | (2006.01) |
| *B01D 11/02* | (2006.01) |
| *B01D 12/00* | (2006.01) |
| *B01D 9/00* | (2006.01) |
| *C08B 30/14* | (2006.01) |
| *C08B 31/00* | (2006.01) |
| *C08J 9/28* | (2006.01) |
| *C08J 9/40* | (2006.01) |
| *C08L 3/04* | (2006.01) |
| *F26B 5/00* | (2006.01) |
| *F26B 5/04* | (2006.01) |

(52) U.S. Cl.
CPC ........ *B01D 11/0203* (2013.01); *A23L 29/212* (2016.08); *A23L 33/11* (2016.08); *A23P 10/00* (2016.08); *A61K 9/5161* (2013.01); *C08B 30/14* (2013.01); *C08B 31/003* (2013.01); *C08J 9/40* (2013.01); *C08L 3/04* (2013.01); *F26B 5/005* (2013.01); *F26B 5/04* (2013.01); *A23L 33/125* (2016.08); *A23V 2002/00* (2013.01); *A61K 47/38* (2013.01); *B01D 9/005* (2013.01); *B01D 12/00* (2013.01); *C08J 9/28* (2013.01); *C08J 2201/036* (2013.01); *C08J 2201/0502* (2013.01); *C08J 2201/0546* (2013.01); *C08J 2205/026* (2013.01); *C08J 2205/042* (2013.01); *C08J 2207/10* (2013.01); *C08J 2303/02* (2013.01)

(58) Field of Classification Search
CPC ...... A23L 29/212; A23L 33/11; A23L 33/125; A23V 2200/25; A23V 2250/2136; A23V 2250/5118; C08J 9/28; C08J 9/40; C08J 2205/042; C08J 2303/02; C08L 3/04
See application file for complete search history.

(56) References Cited

U.S. PATENT DOCUMENTS

| | | | | |
|---|---|---|---|---|
| 5,958,589 A * | 9/1999 | Glenn | .................... | A01N 25/16 106/122 |
| 6,491,952 B1 * | 12/2002 | Sjoberg | .................... | A21D 2/14 424/400 |

OTHER PUBLICATIONS

Ubeyitogullari et al., "Phytosterol nanoparticles with reduced crystallinity generated using nanoporous starch aerogels", Published 2016, RSC Adv., 6, 108319-108327.*
Bufalo et al., Thermal analysis of milling products and its implications in self-ignition; J Therm Anal Calorim, 2014, vol. 115, pp. 1989-1998.
Comin et al., Barley beta-glucan aerogels via supercritical CO2 drying; Food Research International, 2012, vol. 48, pp. 442-448.
Garcia-Gonzalez et al., Use of supercritical fluid technology for the production of tailor-made aerogel prticles for delivery systems; J. of Supercritical Fluids, 2013, vol. 79, pp. 152-158.
Glenn et al., Starch-Based Microcellular Foams; Cereal Chem., vol. 72, No. 2, pp. 155-161.
He et al., A novel chemo-enzymatic synthesis of hydrophilic phytosterol derivatives; Food Chemistry, 2016, vol. 192, pp. 557-565.
Lim et al., phase Equilibria for Carbon Dioxide-Ethanol-Water System at Elevated Pressures; The Journal of Supercritical Fluids, 1994, vol. 7, pp. 219-230.

Joung et al., A phylogenetic analysis of Bacillus thuringiensis sevovars by RFLP-based ribotyping; Journal of Applied Microbiology, 2001, vol. 91, pp. 279-289.

Kenart et al., Automated Label-free Quantification of Metabolites from Liquid Chromatography-Mass Spectrometry Data; Molecular & Cellular Proteomics, vol. 13.1, pp. 348-359.

Liu et al., Preparation of a novel starch-derived three-dimensional ordered macroporous carbon for improving the dissolution rate and oral bioavailability of water-insoluble drugs; Journal of Pharmaceutical and Biomedical Analysis, 2016, vol. 118, pp. 267-275.

Mehling et al., Polysaccharide-based aerogels as drug carriers; Journal of Non-Crystalline Solids, 2009, vol. 355, pp. 2472-2479.

Mel'nikov et al., Effect of phytosterols and phytostanols on the solubilization of cholesterol by dietary mixed micelles: an in vitro study, Chemistry and Physics of Lipids, 2004, vol. 127, pp. 121-141.

Mennah-Govela et al., Mass transport processes n orange-fleshed sweet potatoes leading to structural changes during in vitro gastric digestion; Journal of Food Engineering, 2016, vol. 191, pp. 48-57.

Minekus et al., A standardised static in vitro digestion method suitable for food—an international consensus; Food Funct. 2014, vol. 5, pp. 1113-1124.

(Continued)

*Primary Examiner* — Melissa A Rioja

(57) ABSTRACT

Formation of low-crystallinity phytosterol nanoparticles via cooling-controlled supercritical carbon dioxide (SC—$CO_2$) impregnation of phytosterols into biodegradable nanoporous starch aerogels and methods of preparing these aerogels are disclosed. The nanoporous starch aerogels increase water dissolution and bioaccessibility of the phytosterols, thereby making them available for preparation of high nutraceutical value foods.

5 Claims, 12 Drawing Sheets

(56) References Cited

OTHER PUBLICATIONS

Moreno-Calvo et al., A New Microcrystalline Phytosterol Polymorph Generated Using CO2-Expanded Solvents; Cyst. Growth Des., 2014, vol. 14, pp. 58-68.
Starbird et al., Synthesis of an organic conductive porous material using starch aerogels as template for chronic invasive electrodes; Materials Science and Engineering, 2014, vol. C 37, pp. 177-183.
Turk et al., Stabilized Nanoparticles of Phytosterol by Rapid Expansion From Supercritical Solution Into Aqueous Solution, AAPS PharmSciTech, 2004, vol. 5, No. 4, Article 56 (http://www.aapspharmscitech.org), 10 pages.
Ubeyitogullari et al., Enhancing the bioaccessibility of phytosterols using nanoporous corn and wheat starch bioaerogels, European Journal of Lipid Science and Technology, 37 pages.
Zeng et al., Structural characteristics and physicochemical properties of lotus seed resistant starch prepared by different methods; Food Chemistry, 2015, vol. 186, pp. 213-222.

\* cited by examiner

FIG. 8

Bar chart showing Solubility (wt.%) for Wheat Starch, Aerogel 5%, Aerogel 10%, Aerogel 15%.

FIG. 9

Schematic: Crystalline phytosterol → (SC-CO$_2$) Phytosterol is dissolved in the SC-CO$_2$ and formed solvate complex with SC-CO$_2$ → Diffusion into the nanoporous starch aerogel: Phytosterol and SC-CO$_2$ solvate complexes are entrapped in the nanopores of the starch aerogel → ↓Temperature ↓Pressure: Phytosterols separates from the SC-CO$_2$ and forms colloidal phytosterol particles in the pores.

NANOPOROUS STARCH AEROGELS IMPREGNATED WITH PHYTOSTEROLS AND METHODS OF PREPARING THE NANOPOROUS STARCH AEROGELS

CROSS REFERENCE TO RELATED APPLICATIONS

This application claims the benefit to U.S. Provisional Patent Application No. 62/448,544, filed on Jan. 20, 2017, which is hereby incorporated by reference in its entirety.

BACKGROUND OF THE DISCLOSURE

The present disclosure relates generally to the formation of low-crystallinity phytosterol nanoparticles via cooling-controlled supercritical carbon dioxide (SC—$CO_2$) impregnation into biodegradable nanoporous wheat starch aerogels and methods of preparing these aerogels. Particularly, it has been found that these aerogels and method of impregnation of the aerogels increase the water dissolution and release properties of the phytosterols in the simulated gastric and intestinal fluids, thereby making them available for preparation of high nutraceutical value foods.

In recent years, the concern among food consumers is not simply building blocks and calories, but nutrition for improved health and wellness. The increased prevalence of diet-related illnesses (e.g., obesity, cardiovascular disease, and cancer) and the emerging trend of "green" consumerism have negatively impacted the acceptability of foods containing artificial ingredients. As a result, food industry prioritized the development of foods and beverages using bioactives, e.g. phytosterols, carotenoids, tocopherols, and omega-3 oils, and this has led the food industry to focus on "technology-driven" food products. This means industry and scientists are not just looking for high stability foods, energy food, pre-prepared food, but rather foods enriched with bioactives using various delivery methods to improve the bioavailability and bioefficacy of the bioactives.

Numerous studies have shown the positive health effects of bioactives to maintain health and wellness and also to prevent and cure many diseases. Among lipophilic bioactives, phytosterols has been receiving increasing attention due to growing interest in dietary treatment of hypercholesterolemia. Consequently, there is a growing interest in preparing functional food and nutraceutical products containing phytosterols. Phytosterols, which are chemical homologs of cholesterols, mainly include β-sitosterol, campesterol and stigmasterol. Phytosterols are well-known for their role in reducing the risk of cardiovascular disease by decreasing the serum total and low-density lipoprotein (LDL) cholesterol concentrations in humans. They are further known for managing inflammatory bowel disease (IBD). Recent research has suggested that phytosterols may have other biological activities such as anti-inflammatory, anticancer, and antioxidative effects in addition to cholesterol lowering activity. Nevertheless, the amount of phytosterols taken in the typical Western diet is only 150-400 mg/day. For efficient utilization of phytosterols for their positive health benefits, their content in the diet must be increased. American Heart Association Nutrition Committee suggested consumption of 2 g of phytosterols per day to manage hypercholesterolemia.

Absorption of phytosterols in the body is much smaller compared to cholesterol. During digestion, cholesterol is first incorporated into the dietary mixed micelles for absorption in the intestine. Phytosterols are relatively more hydrophobic than cholesterol and are in dynamic competition with cholesterol for incorporation into dietary mixed micelles, displacing cholesterol and leading to its excretion. Phytosterols are not synthesized in the human body and therefore have to be taken in the diet containing phytosterols such as vegetable oils, nuts, and cereal grains. While there has been a growing trend in the food industry to enrich foods with phytosterols with the growing market demand, food quality can be negatively affected by phytosterols as phytosterols are high melting point crystalline powders, which are not soluble in water and poorly soluble in fats and oils. Thus, conventional phytosterol use has low efficacy, and the crystallization of phytosterols in an oil phase affects food sensory and quality negatively.

Commercially, natural phytosterol mixtures are isolated from vegetable oil deodorizer distillates or tall oil to be used as supplemental sources of phytosterols. However, earlier studies have shown that natural phytosterol mixtures were not very effective in reducing cholesterol as much larger doses were needed. Further, because of the poor solubility and crystallinity of the phytosterols, their inclusion into the micellar phase is limited. Additionally, incorporation of phytosterols into foods is a major challenge from a technological and food quality standpoint because phytosterols are high melting point crystalline powders that are insoluble in water and poorly soluble in fats and oils. When used in this form, the efficacy of the phytosterols is very low, and also crystallization of phytosterols in the oil phase leads to a gritty texture, compromising sensory quality and consumer acceptance.

Based on the foregoing, low water solubility is an important parameter limiting the enrichment of the foods with water-insoluble bioactives. Moreover, water solubility is a key parameter determining the bioavailability of the bioactives. Said a different way, low water solubility limits the health benefits of the bioactives in the food products, and hinders their health benefits due to poor bioavailability caused by poor water solubility. Therefore, improving the bioavailability of bioactive food compounds is essential to improving their bioefficacy. Bioavailability of the lipophilic bioactives also depends on their physical properties such as morphology and crystallinity. Crystalline forms of bioactives are typically less bioavailable than their amorphous or soluble forms. The effect of the crystal structure on the bioavailability was observed for phytosterols. Very low bioavailability of the phytosterols is due to its insoluble crystalline structure.

At present, the main approach to add phytosterols into foods is to esterify the phytosterols with fatty acids to obtain liquid or semi-liquid esters, similar to fats and oils, which can be incorporated into high-fat products like margarines and spreads. However, enrichment of low-fat products is still a challenge. When the big number of low-fat products and the demand for low-fat products are considered, there is a critical need to find solutions to incorporate free phytosterols into foods, including low-fat foods. In order to make the inclusion of the free phytosterols in the foods, it is desirable to have small phytosterol crystals with less crystallinity that can be easily dispersed in water. Emulsion formation, liposomes, and micronization are among the different approaches used to develop delivery forms for phytosterols. Micronization increases the surface-to-volume ratio by decreasing the particle size, leading to increased solubilization and thus increased bioavailability. Microemulsions are suitable only for water-based food formulations, and they require large amounts of surfactants which result in off-flavor formation. They are also sensitive to environmental conditions such as temperature, pH, and dilution. Nanoemulsions are similar in structure to microemulsion, but they are thermodynamically unstable colloidal dispersions and break down over time through a variety of destabilization mechanisms, such as flocculation, coalescence, gravitational separation, and Ostwald ripening. Liposomes are formed of one or more concentric shells of surfactant bilayer. Solvent evaporation method uses organic solvents for liposome production, but clean production is possible with other methods such as extrusion methods. However, short shelf life and low stability are the major problems limiting the use of liposomes in suspension. Therefore, they need to be dried to improve the stability. Another issue is that only few of those systems can be used in the food industry because the materials used to construct the delivery system is not food grade. For a successful commercialization of the delivery system in food industry, the delivery system must be fabricated from food grade ingredients and, possibly, inexpensive ingredients.

SC—$CO_2$ technology has been used as a "green" method for the isolation of phytosterols from various sources, especially fractionation of deodorizers' distillates of vegetable oils. However, the use of supercritical fluid technologies for phytosterol particle engineering is very new. A modified rapid expansion of supercritical solutions (RESS) method was used to form composite L-poly(lactic acid)-phytosterol particles. Another application of supercritical fluid technology for particle formation is DELOS (depressurization of an expanded liquid organic solution). In the DELOS process, the solute is first dissolved in a conventional organic solvent, and $CO_2$ is added to expand the liquid solution at high pressure, and finally the expanded solution is depressurized to form micron size particles. Recently, the DELOS process was used for micronization of phytosterols. However, even though that method generated micron size phytosterols, obtained phytosterol particles had higher crystallinity than the native phytosterol. Moreover, those studies have not demonstrated the improvement of the bioavailability of the generated phytosterol products.

In the present disclosure, a simple and clean approach to decrease the size and crystallinity of the phytosterols in order to improve their bioaccessibility, and in turn bioavailability, is disclosed. This approach uses nanoporous food grade starch as a nanoporous and high surface area mold and SC—$CO_2$ to impregnate the phytosterols into the nanopores and to form colloidal phytosterols with decreased crystallinity.

BRIEF DESCRIPTION OF THE DISCLOSURE

The present disclosure is generally related to nanoporous starch aerogels impregnated with a bioactive. Particularly, low-crystallinity phytosterol nanoparticles are formed using nanoporous starch aerogels via a cooling-controlled SC—$CO_2$ impregnation process. Developing nanoporous starch aerogels impregnated with lipophilic bioactives such as phytosterols will improve the health benefits of the water-insoluble bioactives, will make the addition of crystalline lipophilic bioactives into foods and beverages to produce health and wellness improving foods in a clean and simple way, and maximize the utilization of the bioactives.

Accordingly, in one aspect, the present disclosure is directed to a nanoporous starch aerogel impregnated with a bioactive.

In another aspect, the present disclosure is directed to a method of forming a starch aerogel impregnated with a bioactive, the method comprising: forming a nanoporous starch aerogel; and cooling-controlled impregnating of a supercritical carbon dioxide (SC—$CO_2$)-bioactive solvatocomplex into the nanoporous starch aerogel. In some embodiments, the forming of the nanoporous starch aerogel comprises: forming a starch hydrogel; exchanging water in the starch hydrogel with ethanol to form an alcogel; and SC—$CO_2$ drying the alcogel to form the nanoporous starch aerogel. In some embodiments, the nanoporous starch aerogel can further be ground for use in powder form.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 3B: density (g/cm$^3$)) of wheat starch aerogel monoliths at different gelatinization temperatures and starch concentrations with a mixing rate of 600 rpm. Means that do not share a letter are significantly different.

FIG. 8 is a graph depicting water solubility of wheat starch and aerogels obtained at the selected conditions (gelatinization at 120° C. and 600 rpm; SC—$CO_2$ drying at 40° C., 10 MPa, and 0.5 L/min) with different starch concentrations (5, 10 and 15%). Means that do not share a letter are significantly different.

FIG. 9 depicts the impregnation of phytosterols into the nanoporous starch aerogels (NSAs) using SC—$CO_2$ as done in Example 2.

DETAILED DESCRIPTION

Figure 1:
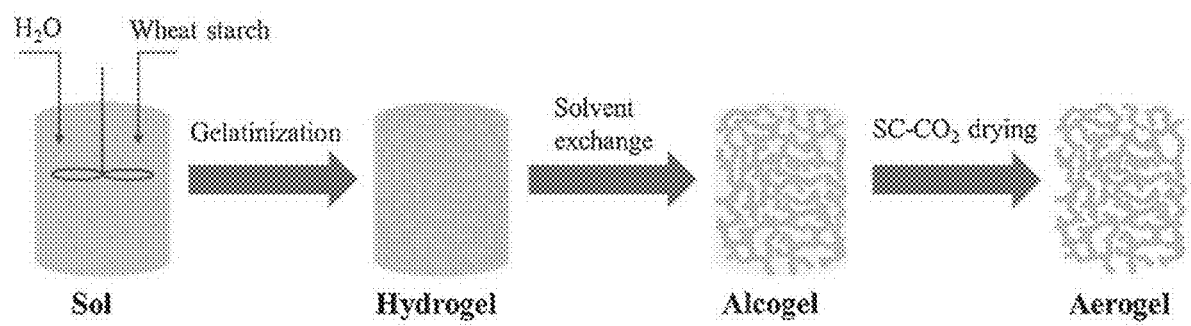
FIG. 1 depicts the main steps involved in the production of aerogels.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

The present disclosure is generally directed to biodegradable nanoporous starch aerogels impregnated with bioactives (e.g., phytosterols) and methods of making and impregnating these aerogels. Aerogels have been attracting a growing interest due to their outstanding surface area, porous structure, and light weight. Aerogels have been investigated for several applications such as thermal insulators, carrier materials, fillers, and filters. The interest in the use of natural, renewable, biodegradable, and biocompatible resources for aerogel formation is growing.

Starch is a promising low cost, renewable, abundant, and bio-based source for aerogel formation. Very recently, formation of corn starch for aerogel formation was reported; however, starch aerogels was not used before to form colloidal particles or to change the crystallinity of bioactives. The present disclosure proposes two innovative approaches, using nanoporous starch aerogels as a material for colloid/nanoparticle formation, and an impregnation method using $SC-CO_2$ to form colloidal phytosterols with reduced crystallinity and in turn enhanced bioavailability.

Suitable starches for use as the starch aerogel in the present disclosure include wheat starch and corn starch. Among starch sources, wheat starch is the third most produced starch type in the world, and it has the potential for the formation of starch hydrogels with three dimensional polymeric network structures and it has an important role in many foods. Wheat starch is comprised of 25% amylose and 75% amylopectin. Amylose is a linear polymer of $\alpha[1\rightarrow4]$ linked D-glucose. On the other hand, amylopectin is a branched polymer with $\alpha[1\rightarrow4]$ and $\alpha[1\rightarrow6]$ bonds and has higher molecular weight than amylose. Currently, wheat has limited uses, mainly for flour production, therefore the use of wheat starch to produce high value aerogel products may maximize the utilization of wheat and add value to wheat. Wheat starch aerogels with their outstanding properties will provide many opportunities for food applications, and bioactive protection and delivery. Accordingly, in one particularly suitable embodiment, the starch aerogel is wheat starch aerogel.

As used herein, the starch aerogels are nanoporous. As used herein, "nanoporous" refers to aerogels having a regular, porous structure, where the size of the pores is generally 100 nanometers or smaller. The nanopores of the Nanoporous starch aerogel (NSA) act as a mold to prevent the formation of bigger phytosterol crystals and lead to the formation of phytosterol nanoparticles whilst decreasing their crystallinity, which later leads to the enhanced solubility of the phytosterols in water and gastrointestinal fluid, thus, enhancing the phytosterols bioassessibility and bioavailability when used in the food industry. As described more fully in the Examples below, the impregnated phytosterols were 37 times more soluble than the crude phytosterols in water.

The starch aerogels are impregnated with bioactives. In one embodiment, suitable bioactives include phytosterols. Suitable phytosterols include, for example, β-sitosterol, campesterol, stigmasterol, and combinations thereof.

In accordance with another embodiment of the present disclosure, methods of forming the nanoporous starch aerogels and use of the formed aerogels for impregnation of bioactives are disclosed. Typically, the method of forming a starch aerogel impregnated with a bioactive includes: forming a nanoporous starch aerogel; and cooling-controlled impregnating of a supercritical carbon dioxide ($SC-CO_2$)-bioactive solvato-complex into the nanoporous starch aerogel.

To form the nanoporous starch aerogel, the methods of the present disclosure include: forming a starch hydrogel; exchanging water in the starch hydrogel with ethanol to form an alcogel; and $SC-CO_2$ drying the alcogel to form the nanoporous starch aerogel.

The starch hydrogel is typically formed by gelatinizing starch. For example, in one embodiment, the starch is gelatinized at a temperature ranging from about 80° C. to about 140° C. to form a three-dimensional starch hydrogel. The starch hydrogel suitably includes from about 5% to about 15% by weight starch, and suitably, about 10% by weight starch.

To form an alcogel, the methods include exchanging water in the starch hydrogel with ethanol by immersing the starch hydrogel in an ethanol solution. In one suitable embodiment, the ethanol solution includes from about 30% v/v to 100% v/v ethanol. The immersion of the starch hydrogel can occur in one solution of ethanol or multiple solutions of ethanol. Further, the ethanol solutions can vary in ethanol concentration. The starch hydrogels are immersed for a time period of from about 30 minutes to about 48 hours, and suitably from about 1 hour to about 24 hours. For example, in one particularly suitable embodiment, the starch hydrogel is immersed in a first ethanol solution comprising about 30% v/v ethanol for a first time period of about 1 hour, the starch hydrogel is immersed in a second ethanol solution comprising about 50% v/v ethanol for a second time period of about 1 hour, the starch hydrogel is immersed in a third ethanol solution comprising about 70% v/v ethanol for a third time period of about 1 hour, the starch hydrogel is immersed in a fourth ethanol solution comprising 100% v/v ethanol for a fourth time period of about 1 hour, and the starch hydrogel is immersed in a fifth ethanol solution comprising 100% v/v ethanol for a fifth time period of about 24 hours.

Supercritical fluid technology, and particularly, $SC-CO_2$ has proven itself as an efficient and environmentally friendly technology and has found use in the extraction of lipids from a variety of natural materials, and, in particle formation as a new promising application of supercritical fluids. Particularly, $SC-CO_2$ is used as a solvent for lipid and lipophilic bioactive extraction, medium for enzymatic reactions, atomizer for micro- and nanoparticle formation, dryer for aerogel formation, and solvent/carrier for impregnation. Unique tunable properties, and advantages of nontoxicity, nonflammability, low cost, availability in large quantities, tunable solvent properties, and moderate critical temperature and pressure of $SC-CO_2$ allow for the development of green methods and products that cannot be possible with conventional technologies. Generally, the $SC-CO_2$ drying of the alcogel to form the aerogel includes $SC-CO_2$ extraction as known in the $SC-CO_2$ drying art.

Accordingly, once the aerogel is formed, the methods of the present disclosure further include impregnating a $SC-CO_2$-bioactive solvato-complex into the nanoporous starch aerogel powder by: $SC-CO_2$ dissolving the bioactive to form the $SC-CO_2$-bioactive solvato-complex; and cooling the $SC-CO_2$-bioactive solvato-complex to room temperature to precipitate the bioactive from the $SC-CO_2$ into the nanoporous starch aerogel. In one embodiment, the bioactive is $SC-CO_2$ dissolved at a temperature of about least 31° C. and a pressure at least 10 MPa to form the $SC-CO_2$-bioactive solvato-complex. In one particularly suitable embodiment, the bioactive is $SC-CO_2$ dissolved at a temperature of about 70° C. and a pressure of about 45 MPa to form the $SC-CO_2$-bioactive solvato-complex. In one embodiment, the $SC-CO_2$-bioactive solvato-complex is cooled to at or below room temperature, and suitably, at room temperature, to precipitate the bioactive from the $SC-CO_2$ into the nanoporous starch aerogel.

In some embodiments, the methods further include grinding the nanoporous starch aerogel into a nanoporous starch aerogel powder. That is, as formed, the nanoporous starch aerogel is typically cylindrical in shape. The cylindrical shaped nanoporous starch aerogels can be impregnated with the $SC-CO_2$-bioactive solvato-complex and used as is, or, after impregnation, can be further ground into a powder form for end use.

The following examples and procedures further illustrate specific embodiments of the invention; however, the following illustrative examples should not be interpreted in any way to limit the invention.

EXAMPLES

Example 1

In this Example, biodegradable high surface area and nanoporous aerogels were prepared from wheat starch. The aerogel formation parameters, namely, starch concentration, gelatinization temperature, and mixing rate during gelatinization; $SC-CO_2$ drying conditions, namely, temperature, pressure, and flow rate of $CO_2$; and the wheat starch aerogel formation conditions for the highest surface area and smallest pore size were investigated.

Materials and Methods

Materials

Wheat starch was obtained from Manildra Milling Corporation (IA, USA). Carbon dioxide (99.99% purity) was supplied by Matheson Tri-Gas, Inc. (PA, USA), and ethanol (100%) was purchased from Decon Laboratories, Inc. (PA, USA).

Aerogel Formation

Production steps of the aerogels are illustrated in FIG. 1. The starch solution was converted into hydrogel by gelatinization, and the hydrogel was converted to alcogel by solvent exchange, and finally the alcogel was converted to aerogel by $SC-CO_2$ drying. Details of each step are given below.

Hydrogel Formation

Hydrogel monoliths were formed according to the method of García-González and Smirnova (2013) with some modifications (FIG. 1). Wheat starch was gelatinized using temperature as a physical cross-linker in a high pressure reactor (4520 Bench Top Reactor, Parr Instrument Company, IL, USA) equipped with two 6-blade impellers and the reactor was heated with a ceramic heater and the temperature was controlled with a temperature controller (4848, Parr Instrument Company, IL, USA). The reactor was cooled with a cooling coil inserted into the reactor. Wheat starch dispersions (5, 10, and 15%, w/w) were mixed in the reactor at a mixing rate of 600 rpm for 5 minutes at room temperature (21° C.). Different mixing rates (200 and 300 rpm) were also studied during gelatinization. Starch dispersion was heated to the predetermined set gelatinization temperatures (100, 120, 130, and 140° C.) and stirred at 600 rpm for 20 minutes at the set temperature. Then, the temperature was decreased to 80° C. at the same stirring rate. After the pressure (around 0.1 MPa) built in the vessel due to water vapor released, stirrer was stopped, then the vessel was removed, and the gel was poured into cylindrical polypropylene molds (1.5 cm diameter and 9 cm length). Polypropylene molds were used; because, it has less surface irregularities than other molds e.g. glass molds. Then, the molds were sealed with parafilm to prevent water loss, and the samples were placed in the fridge at 4° C. for 48 hours for retrogradation.

Solvent Exchange

After the retrogradation, the hydrogels were removed from the molds and cut into monoliths of 2 cm length. Alcogels were formed by replacing the water in the monoliths with ethanol using a five-step solvent exchange procedure by soaking hydrogel monoliths in 30, 50, 70, and 100% (v/v) ethanol for 1 hour residence time, and 100% ethanol for 24 hours (Perez-Cantu, Liebner, & Smirnova, 2014) (FIG. 1).

Xerogel and Aerogel Formation

Xerogels were obtained by air drying of the alcogels under the fume hood at room temperature until a constant weight was reached. Aerogels were obtained with removing the ethanol in the monoliths with $SC-CO_2$ in a laboratory scale $SC-CO_2$ extraction system (SFT-110, Supercritical Fluids, Inc., DE, USA). Details of the $SC-CO_2$ extraction system are provided in Belayneh, Wehling, Cahoon, & Ciftci, 2015. The extraction vessel temperature (40 and 50° C.) and restrictor block temperature (80° C.) were set prior to the experiment. $SC-CO_2$ drying temperatures were selected based on literature (García-González & Smirnova, 2013; Comin et al., 2012) and then those conditions were verified in preliminary studies (data not shown). The alcogels were placed into a custom-made perforated (0.002 mm hole diameter) polypropylene basket (8.5 cm height and 2.7 cm diameter). A stainless steel frit was placed on top of the perforated section of the basket, and the alcogels were placed on the frit. Excess amount of ethanol was added into the basket, and the basket was placed into the 100 mL extraction vessel. The perforated basket with the frit allowed for keeping the ethanol in the basket until drying and to enable the SC—$CO_2$ to flow into the basket. Excess amount of ethanol was added into the extraction vessel to prevent shrinkage in the aerogels that is caused by evaporation of ethanol from the alcogel before the supercritical conditions were reached and glass wool was placed on top of the basket to keep the alcogels immersed in ethanol. The system was pressurized with $CO_2$ (10 and 15 MPa) using the high pressure pump and kept at constant set pressure and temperature for 10 minutes. SC—$CO_2$ drying pressures were selected based on literature (García-González & Smirnova, 2013; Kenar et al., 2014; Comin et al., 2012) and then those conditions were verified in preliminary studies (data not shown). $CO_2$ flow rate was adjusted to 1 L/min (measured at ambient conditions) and maintained constant using the micrometering valve during 4 hours of drying. $CO_2$ flow rates of 0.5 and 1.5 L/min were also investigated. Drying time was kept constant at 4 hours at all pressure and temperatures considering the solubility of ethanol in the SC—$CO_2$ at those conditions and was verified in preliminary studies by oven drying of the aerogels at 105° C. for 2 hours (data not shown) that more than 96% of the ethanol was removed even at the lowest solubility of ethanol in SC—$CO_2$ (5%, w/w) at 10 MPa and 40° C. (Joung et al., 2001; Lim, Lee, & Chun, 1994). After 4 hours of drying, the system was depressurized at the same $CO_2$ flow rate and temperature. Finally, samples were collected and stored at room temperature until characterized. The dimensions of the xerogels and aerogels before and after drying were measured using a caliper (H134150000, Bel-Art Products, NJ, USA) with a precision of 0.05 mm. Weight of SC—$CO_2$-dried gels (aerogel) were determined using an electronic balance (ME204E, Mettler Toledo, Ohio, USA) with a precision of 0.0001 g. All experiments were conducted in duplicate.

Characterization

Surface Area, Pore Size, and Pore Volume

Brunauer-Emmett-Teller (BET) surface area and Barrett-Joyner-Halenda (BJH) pore size and pore volume of the xerogel and aerogel samples were determined using low-temperature nitrogen adsorption-desorption analysis (ASAP 2020, Micromeritics Instrument Corporation, GA, USA). Samples (0.06-0.3 g) were cut into small pieces to fit in the sample tube, and degassed under vacuum at 115° C. for 4 hours prior to analysis (Comin et al., 2012). Nitrogen sorption experiments were conducted at −196° C. Specific surface area was determined by multipoint BET adsorption characteristics at a relative pressure (p/$p_0$; equilibrium pressure of nitrogen at the sample surface/saturation pressure of nitrogen) between 0.05 and 0.3. In the same manner, pore volume and pore size distribution were evaluated at a relative pressure of p/$p_0$>0.35. The overall pore volume was reported based on the BJH adsorption cumulative volume of pores between 1.7 nm and 300 nm width.

Morphology

The morphology of the xerogels and aerogels was analyzed by the field emission scanning electron microscope (S4700 FE-SEM, Hitachi, Tokyo, Japan) at 5 kV and 15 mA under low vacuum mode. The specimens were prepared by cutting 1-mm thick cross-sections from the monoliths and placed on aluminum SEM specimen stubs with double-side conductive carbon tape. The samples were sputter-coated with a chromium layer (DeskV HP TSC, Denton Vacuum LLC, NJ, USA) prior to analysis.

Crystallinity

Crystallinity of the samples was studied with X-ray diffraction (XRD) analysis using a PANalytical Empyrean Diffractometer (Empyrean, PANalytical B.V., Almelo, Netherlands) equipped with PIXcel3D detector. The detector was operated with 1D detection. The diffractometer was operated at 45 kV, 40 mA with Cu Ka beam monochromator. The samples were ground and sieved through 0.85 mm screen (mesh #20) before the analysis. The powdered samples were spread on the sample holder and were spun continuously at the rate of 3.75 rpm throughout the analysis. The samples were scanned within the range of 2-40° (2Θ) with a step size of 0.050 at a scanning speed of 1.267/min.

Percent degree of crystallinity was calculated using the equation below:

$$\text{Degree of crystallinity}(\%) = \frac{A_c}{A_c + A_a} \times 100 \quad (1)$$

where $A_c$ is the area of the crystalline part, and $A_a$ is the area of the amorphous part. Software OriginPro 2016 (OriginLab Corporation, Northampton, Mass., USA) was used for the calculation of the area under the relevant curves (Muljana, Picchioni, Heeres, & Janssen, 2009).

Water Solubility

The water solubility of wheat starch and wheat starch aerogels was determined according to Ayoub and Rizvi (2008). One gram of powdered sample was dispersed in 100 mL of distilled water. Then the dispersion was heated to 60° C. and kept at that temperature for 10 minutes in a water bath. Then, the dispersion was centrifuged at 670 g for 20 minutes (Clinical 200, VWR International, Radnor, Pa., USA). Known amount of supernatant was dried at 103° C. until a constant weight was reached in an aluminum pan. The solubility was calculated according to the following equation:

$$\text{Solubility (wt. \%)} = \frac{\text{weight of dissolved solids in supernatant}}{\text{weight of sample}} \times 100 \quad (2)$$

Thermal Stability

Thermal gravimetric analysis (TGA) of the samples was performed in a TG 209 F1 Libra Thermogravimetric Analyzer (TG 209 F1 Libra, NETZSCH, Selb, Germany). Each sample (5-10 mg) was placed in a sealed aluminum pan and heated from room temperature to 600° C. at a heating rate of 10° C./min under a nitrogen atmosphere with a gas flow of 20 mL/min. Prior to analysis, the furnace was vacuumed. Percent weight loss with temperature was monitored for each sample.

Statistical Analysis

Statistical evaluation of the results was performed using Minitab® 16.1.1 software (Minitab Inc., State Collage, Pa., USA). Multiple comparison of the means was carried out by Tukey test at a=0.05 level.

Figure 2:
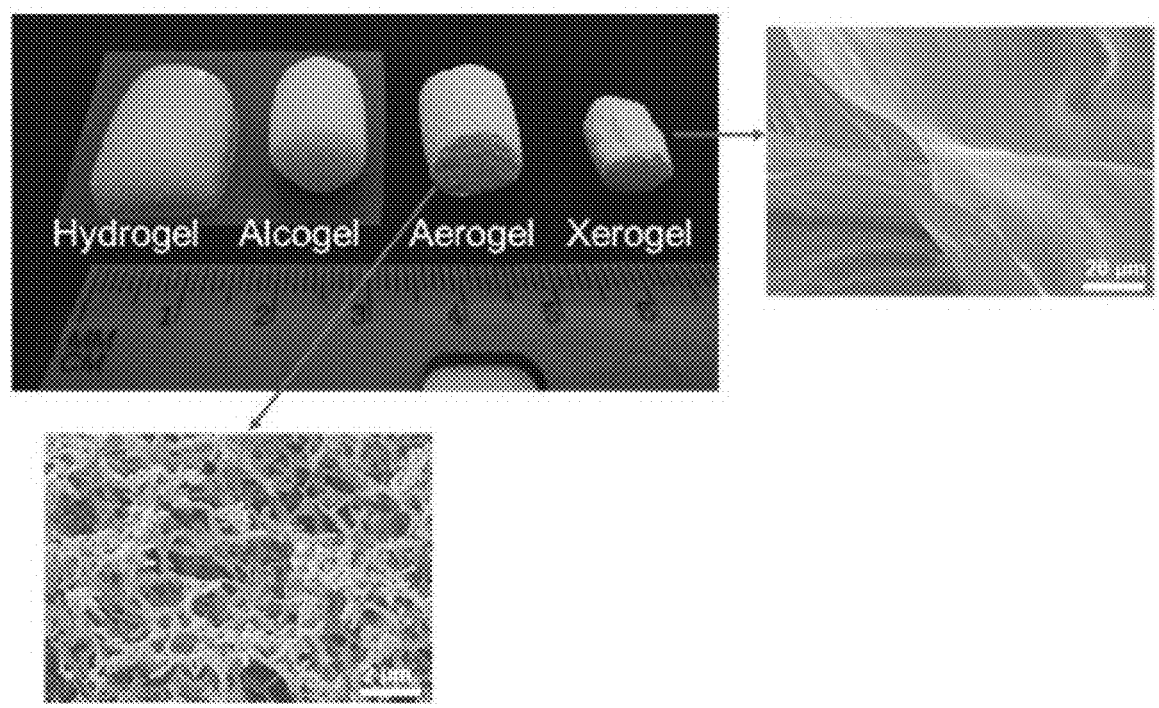
FIG. 2 depicts the hydrogel, alcogel, aerogel and xerogel formed from wheat starch in Example 1.

Results and Discussion
 Effect of Drying Technique
 Water removal from the structure to form a porous structure is very crucial due to high surface tension and capillary forces in the pores, which cause collapse of the porous structure. Air drying of the alcogels led to a high shrinkage rate in the xerogels due to high surface tension and capillary pressure gradient in the pores (FIG. 2). Moreover, the SEM images revealed that the structure of xerogel is nonporous (FIG. 2), and the BET surface area of the xerogels was lower than 0.05 $m^2/g$. Therefore, air drying was not further studied, and all aerogels were formed by SC—$CO_2$ drying, which resulted in a porous structure.

Shrinkage

Figure 3A:
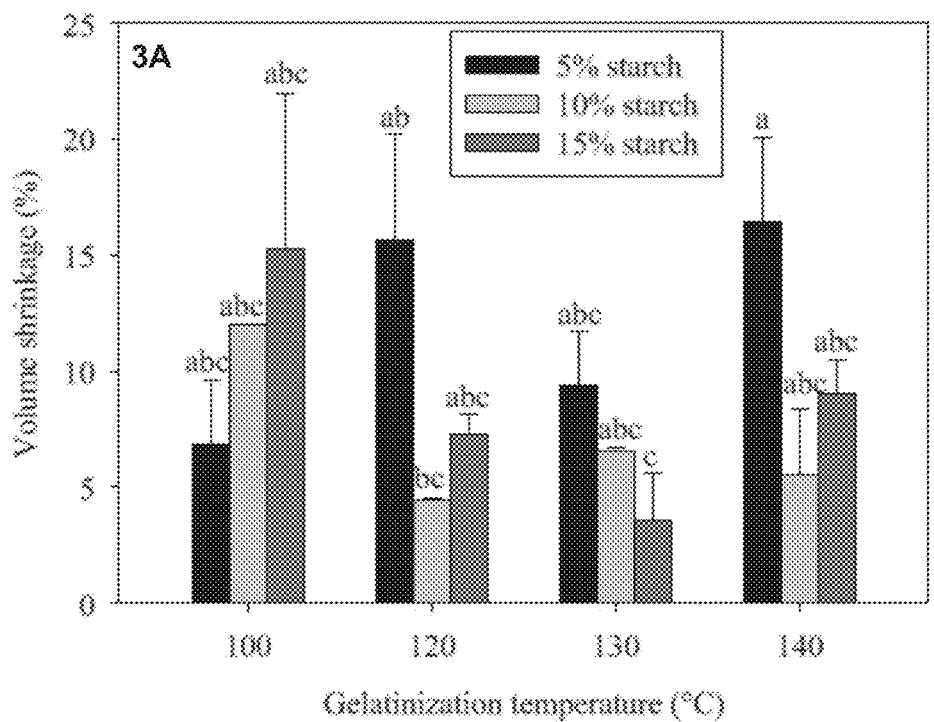
FIGS. 3A & 3B depict physical properties (FIG. 3A: volume shrinkage (%)

FIG. 3A shows the volume shrinkage of aerogels dried with SC—$CO_2$ at 40° C. and 10 MPa for 4 hours with a $CO_2$ flow rate of 1 L/min. There was a significant decrease in the shrinkage as the starch concentration increased from 5 to 15% at all temperatures other than 100° C. ($p<0.05$). The highest shrinkage was observed at 15% starch concentration at 100° C. (15.3%), and at 5% starch concentration at 120, 130, and 140° C. (9.4-16.4%), whereas the lowest was at starch concentrations of 10 and 15% at 120 and 130° C. (3.6-7.3%). In this study, wheat starch aerogels (6.9-16.4%) exhibited lower shrinkage compared to the barley beta-glucan aerogels (23%) obtained at the same 5% concentration by Comin et al. (2012). Moreover, the lowest volume shrinkage of corn starch aerogels (18%) obtained by Kenar et al. (2014) was higher than wheat starch aerogels (3.6%) conducted at 130° C. and 15% starch concentration. The different trend at 100° C. compared to higher temperatures was due to lack of proper gelatinization. Moreover, the swelling degree is lower at high starch concentrations, which increases the strength of the gel. Higher starch concentrations create mechanically strong gels that may have less shrinkage.

Density

Figure 3B:
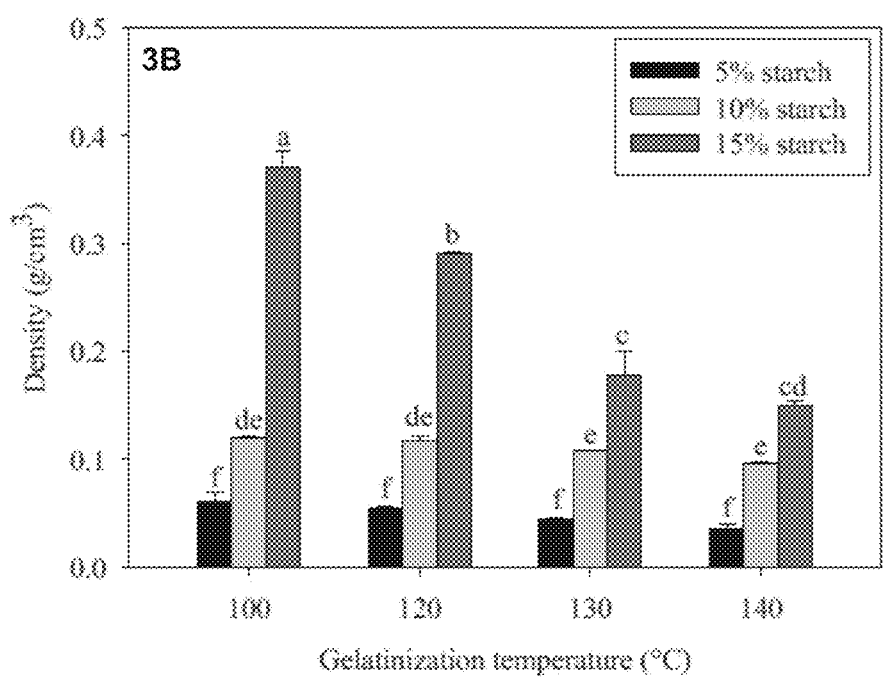

As the gelatinization temperature increased, the density decreased at all starch concentrations (FIG. 3b). Although the decrease was not significant at 5% starch concentration ($p>0.05$), it was significant at the highest level of the starch concentration ($p<0.05$) as the temperature increased to 130° C. This decrease in density was due to higher gelatinization degree and formation of more fibrous starch network at higher gelatinization temperatures. Lowest densities were obtained at 120 (0.05 $g/cm^3$), 130 (0.04 $g/cm^3$), and 140° C. (0.03 $g/cm^3$), and there was no significant difference between those densities ($p>0.05$).

García-González and Smirnova (2013) also reported that the densities of corn and pea starch aerogels increased as the starch concentration increased from 7 to 15% and they reported the lowest density of 0.15 $g/cm^3$ at 7% corn starch. Wheat starch-based microcellular foams obtained at 8% concentration had a density of 0.23 $g/cm^3$ (Glenn & Irving, 1995), which is almost six times higher than the density obtained in the instant Example at the starch concentration of 5%. Lower aerogel densities offer advantages depending on the end use; e.g., lower caloric value and less starch consumption if used in a food preparation to give texture.

Surface Area

Figures 4A, 4B:
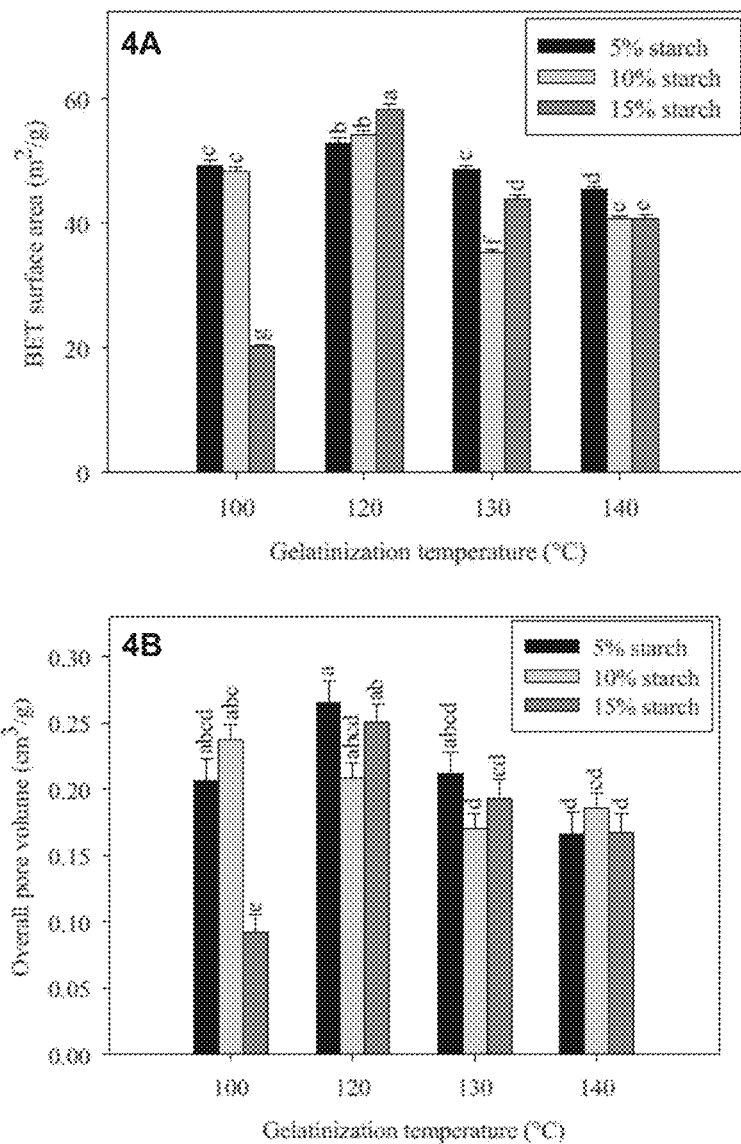
FIGS. 4A-4C depict the effect of the gelatinization temperature (100, 120, 130 and 140° C.) and wheat starch concentration (5, 10 and 15%) on: surface area (m2/g) (FIG. 4A); overall pore volume (cm3/g) (FIG. 4B); and average pore size (nm) (FIG. 4C). Means that do not share a letter are significantly different.

The surface area seemed not to have any relationship with the starch concentration (FIG. 4A). Gelatinization temperature of 100° C. had a different pattern compared to the others due to improper gelatinization. Surface areas of 49.4 and 48.4 $m^2/g$ were obtained at 5 and 10% starch concentration, respectively; however, it decreased to 20.2 $m^2/g$ when the starch concentration was increased to 15%. Increasing the gelatinization temperature to 120° C. resulted in an increase in the surface area, which is related to the reduction in remnants of starch granules and forming a better network structure (Atkin, Abeysekera, & Robards, 1998). The highest surface area (58.3 $m^2/g$) was obtained with 15% starch concentration at 120° C. Increasing temperature beyond 120° C. led to a decrease in the surface area of the starch aerogels (FIG. 4A). Surface area was 48.7 and 45.4 $m^2/g$ at 5% starch concentration at 130 and 140° C., respectively. Having a maximum at 120° C. and decreasing surface area with further increase in the temperature could be explained by bursting of the swollen starch granules and collapsing the structure when the temperature was further increased.

Pore Size and Pore Volume

Figure 4C:
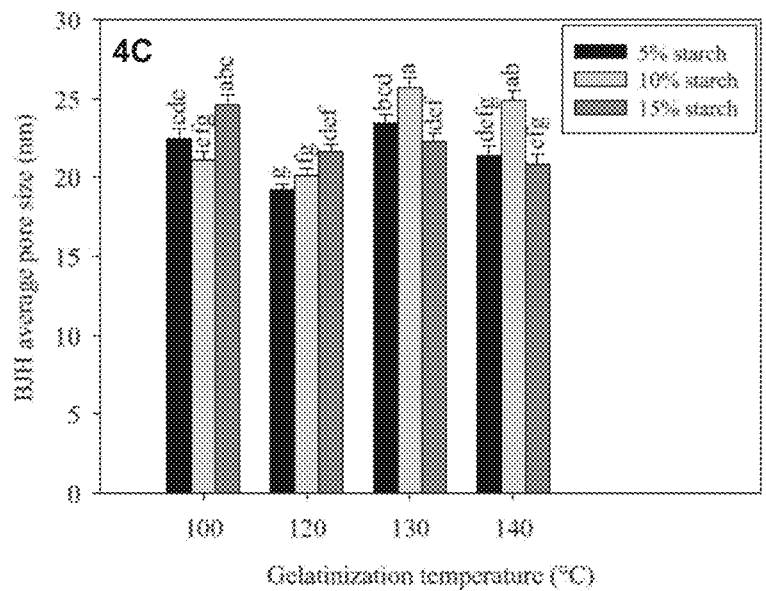

Overall pore volume had the same pattern with the surface area data and the overall pore volume was distributed in between 0.09 (100° C. and 15% starch) and 0.27 $cm^3/g$ (120° C. and 5% starch) (FIG. 4B). Having high pore volume resulted in higher surface area, but the pore size was also effective on the surface area of the aerogels. The smallest pore size of 19.2 nm was obtained at gelatinization temperature of 120° C. and starch concentration of 5% (FIG. 4C).

Process Parameters for Aerogel Formation

The process parameters were analyzed at 10% starch concentration and 120° C. gelatinization temperature, and the effects of other process parameters, namely, mixing rate during gelatinization, flow rate of $CO_2$ during SC—$CO_2$ drying, SC—$CO_2$ drying temperature, and SC—$CO_2$ pressure were investigated. At higher mixing rate (600 rpm), higher surface area was obtained due to improved distribution of starch granules and having less granule remnants with high shear at a constant mixing time of 20 minutes.

Figure 5:
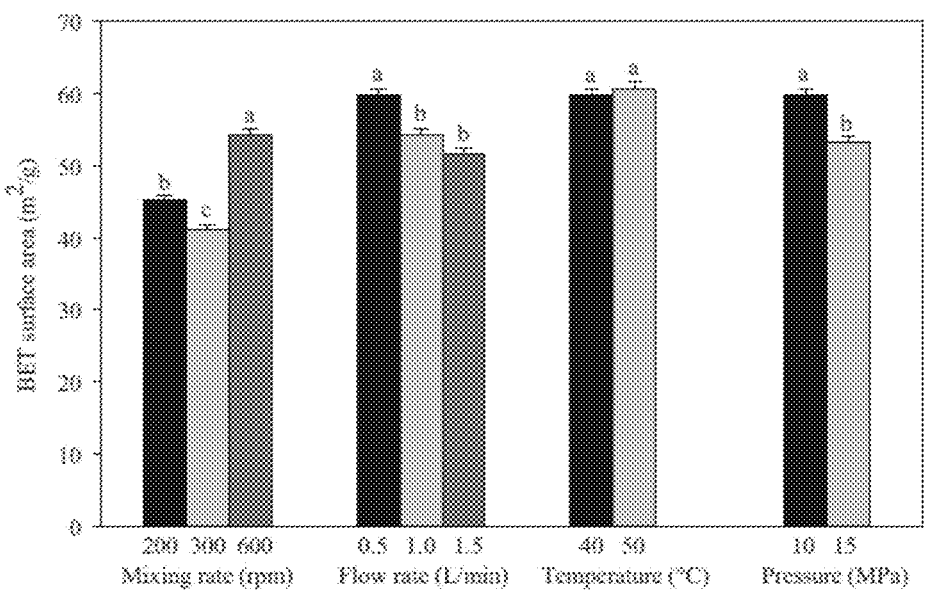
FIG. 5 depicts the effect of processing parameters (mixing rate (200, 300 and 600 rpm) during gelatinization, and flow rate of $CO_2$ (0.5, 1 and 1.5 L/min), temperature (40 and 50° C.), and pressure (10 and 15 MPa)) during SC—$CO_2$ drying on surface area (m$^2$/g) of 10% wheat starch aerogels. Means within each parameter that do not share a letter are significantly different.

The increase in the $CO_2$ flow rate from 0.5 L/min to 1.5 L/min during SC—$CO_2$ drying decreased the surface area from 59.7 to 51.6 $m^2/g$ (FIG. 5). Drying of alcogels at high $CO_2$ flow rate makes the convective mass transfer more effective, and therefore high convective mass flux of ethanol from alcogel resulted in a decrease in the surface area due to the expanded liquid in pores with high dissolution of SC—$CO_2$ in ethanol. Thus, the highest surface area was obtained at lowest flow rate of 0.5 L/min where lower convection rate was expected.

SC—$CO_2$ drying temperature and pressure were also effective on the surface area (FIG. 5). The solubility of ethanol in SC—$CO_2$ increases with temperature and pressure. Increase in the temperature did not have a significant effect on the surface area ($p>0.05$). However, both temperature and pressure affected the surface area due to solubility of ethanol in SC—$CO_2$ and mass transfer related properties. Even though the solubility of ethanol in SC—$CO_2$ increases with pressure, density of the SC—$CO_2$ and ethanol mixture also increases, which effects the diffusion properties negatively; therefore, surface area decreased from 59.7 $m^2/g$ at 40° C. and 10 MPa to 53.1 $m^2/g$ at 40° C. and 15 MPa. Based on the surface area data and energy consumption and process economics concerns, alcogel drying conditions were selected as 40° C. and 10 MPa. $CO_2$ is in supercritical state at all employed temperature and pressure combinations, and it formed a mixture with $CO_2$-expanded ethanol. This mixture is at the vapor-liquid equilibria of the $CO_2$-ethanol.

Finally, the aerogels were produced at conditions (gelatinization temperature: 120° C., mixing rate: 600 rpm, $CO_2$ flow rate: 0.5 L/min, SC—$CO_2$ drying temperature: 40° C. and pressure: 10 MPa) with different wheat starch concentrations. Surface area of the aerogels obtained with starch concentrations of 5, 10, and 15% were 53.5, 59.7 and 52.6 m²/g, respectively. At these conditions, the overall pore volume and average pore size were in the range of 0.21-0.27 cm³/g, and 16.0-20.2 nm, respectively. The surface area depends on the starch source. A study carried out by Glenn & Stern (1999) reported wheat starch based micro-cellular foam with a higher surface area (116 m²/g), but the surface area of the corn starch aerogel was lower (50 m²/g). The highest surface area (362 m²/g) of high amylose corn starch aerogels was reported by Kenar et al. (2014). Potato and Amylomaize VII starch with an apparent amylose content of 75% (Eurylon 7) starch had surface area of 72.5 and 90.3 m²/g (Mehling et al., 2009). Having lower surface areas with wheat starch could be due to different swelling properties of the wheat starch. Moreover, the molecular weight of the wheat starch is higher than that of corn starch in terms of both amylose and amylopectin components. High molecular weight affected the structure network and resulted in lower surface area.

Further Characterization of the Wheat Starch Aerogels Obtained at the Analyzed Conditions Morphology All aerogels had three dimensional open porous structures (FIGS. 6A-6F), and the structures became denser at higher starch concentrations because of the decrease in sizes of the network openings (FIGS. 6B, 6C, 6E and 6F). That also explains the density data which increased with concentration (FIG. 3B).

Figures 6A, 6B, 6C, 6D, 6E, 6F:
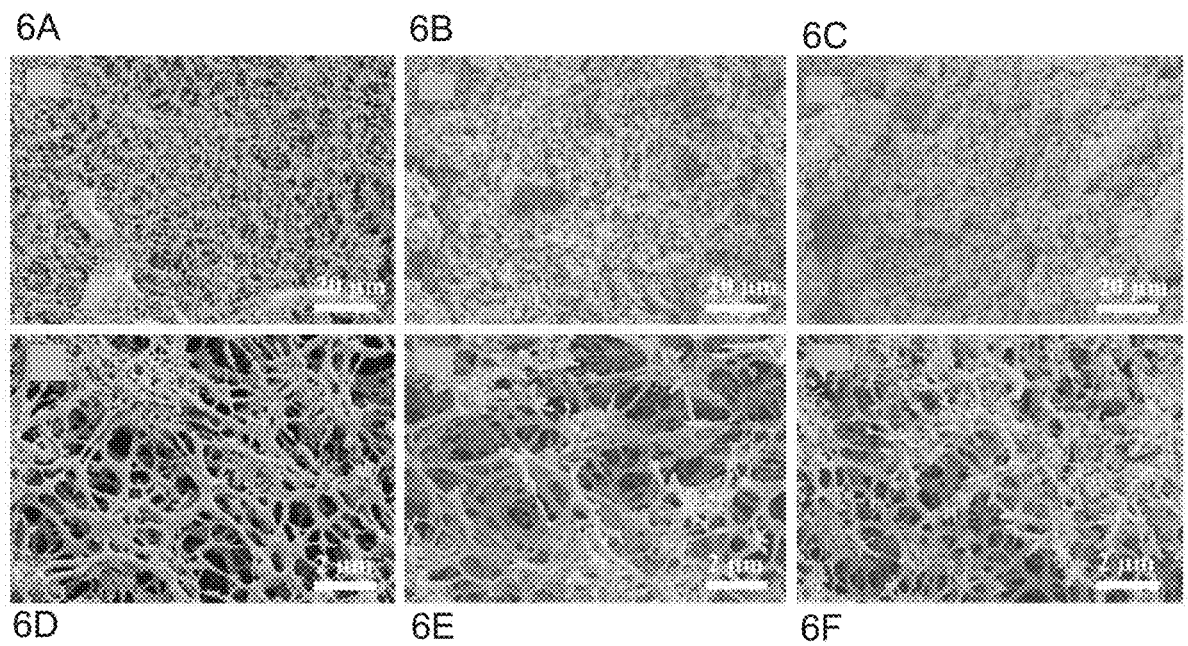
FIGS. 6A-6F depict low and high magnification SEM micrographs of wheat starch aerogels obtained at the selected conditions with starch concentrations of 5% (FIGS. 6A & 6D), 10% (FIGS. 6B & 6E) and 15% (FIGS. 6C & 6F).

The structure was mostly composed of interconnected fibrils with approximately 150-400 nm thickness and nanopores (FIGS. 6D-6F). The nanoporous structure was also confirmed with BJH average pore size data depicted in FIG. 4C. Similar nanoporous structure was reported for corn and pea starch aerogels by Garcia-González & Smirnova, 2013; Starbird, García-González, Smirnova, Krautschneider, & Bauhofer, 2014. However, wheat starch foams studied by Glenn & Irving (1995) were less porous and had non-homogeneous network structures.

Crystallinity

Figure 7:
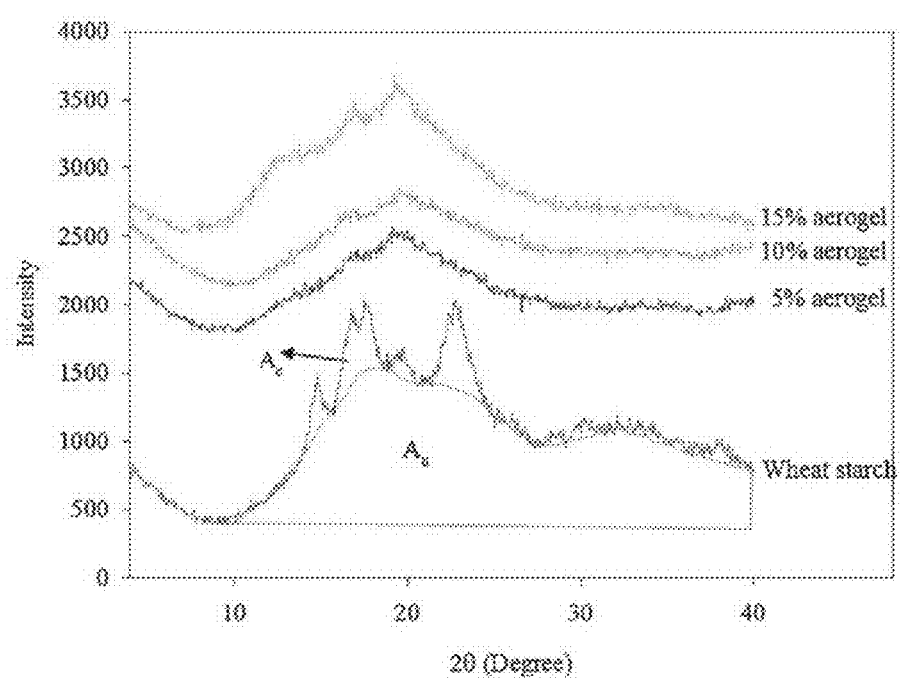
FIG. 7 depicts x-ray diffraction (XRD) patterns of the wheat starch and aerogels obtained at the analyzed conditions of Example 1 (gelatinization at 120° C. and 600 rpm; SC—$CO_2$ drying at 40° C., 10 MPa and 0.5 L/min) with different starch concentrations (5, 10 and 15%) where $A_c$ is the crystalline region and $A_a$ is the amorphous region.

XRD patterns presenting the crystallinity of the wheat starch and aerogels obtained at the analyzed production conditions are shown in FIG. 7. Wheat starch had five strong diffraction peaks at $2\Theta=14.80$, $16.7°$, $17.5°$, $19.6°$, and $22.7°$, respectively, which indicates the crystalline part of the wheat starch. However, these peaks were not observed in aerogels due to gelatinization of the wheat starch. Based on the crystalline and amorphous regions given in FIG. 7, the degree of crystallinity of aerogels with 5, 10, and 15% starch concentration was calculated as 5, 5, and 7%, respectively. The wheat starch had a degree of crystallinity of 20% which is in agreement with the findings of Ratnayake and Jackson (2007).

Water Solubility

Solubility of the wheat starch was 0.9%, whereas the solubility of the aerogels with 5 and 10% starch concentration were 2.7 and 2.4%, respectively (FIG. 8). There was no significant difference between the solubility of the aerogels with 5 and 10% starch concentration (p>0.05), but the solubility of aerogel with 15% starch concentration (1.7%, w/w) was significantly lower (p<0.05) (FIG. 8). The solubility in water increased with the increase in the amorphous part of the sample, which is related to the high free energy of the amorphous structure. A similar relationship was reported for lotus seed resistant starch (Zeng et al., 2015).

Thermal Stability

TGA curves of the wheat starch and wheat starch aerogels exhibited a similar pattern. There was a rapid thermal degradation of both samples in the range of 280-330° C., which is called as active pyrolysis zone. At that temperature range, there was 51% and 55% decrease in the weight of wheat starch aerogels and wheat starch, respectively. These observations were in good agreement with the results of Bufalo, Costagliola, Mosca, and Ambrosone (2014) where the wheat starch had a main degradation temperature between 240 and 320° C. However, the residual mass (char+ash) of wheat starch aerogel (17%) was slightly higher than that of the wheat starch (13%) at 600° C. That difference indicates faster rate of formation of char and ash in aerogels. Wheat starch aerogels with different starch concentrations (5, 10 and 15%) exhibited similar TGA curves.

Biodegradable nanoporous wheat starch aerogels were successfully produced using SC—$CO_2$ drying. The highest BET surface area of 59.7 m²/g was achieved with gelatinization of 10% wheat starch at 120° C. and 600 rpm and SC—$CO_2$ drying at 40° C. and 10 MPa with $CO_2$ flow rate of 0.5 L/min. Concentration of wheat starch did not drastically affect the surface area of the aerogels. Crystallinity of the samples was in good agreement with the solubility data; solubility in water increased with decreasing crystallinity. The thermal stability of the wheat starch aerogels was not different than that of the wheat starch.

These wheat starch aerogels with large surface area, nanoporous structure, and ultra-low density can be used for several purposes such as bioactive carriers, fillers in food preparations, and solid supports for biocatalysts.

Example 2

In this Example, the method of the present disclosure was used to decrease the size and crystallinity of phytosterols in order to enhance their solubility and, consequently, their bioavailability. Specific objectives were as follows: (a) fabricate and characterize nanoporous starch aerogels (NSAs), (b) generate phytosterol nanoparticles with decreased crystallinity by impregnating the phytosterols into the NSAs using the green SC—$CO_2$ impregnation method of the present disclosure, and (c) determine the solubility (dispersibility) of the phytosterols impregnated into the NSAs in water and simulated gastrointestinal fluid.

Materials and Methods

Wheat starch was provided by Manildra Milling Corporation (IA, USA). Crude phytosterols were purchased from MP Biomedicals (OH, USA). Composition of crude phytosterols was determined by gas chromatography-mass spectrometry (GC-MS) and found to be 52.8%±0.5% b-sitosterol, 24.3%±0.1% stigmasterol and 22.9%±0.6% campesterol. High purity (99.99%) liquid $CO_2$ was purchased from Matheson Tri-Gas, Inc. (PA, USA), and ethanol (100%) was purchased from Decon Laboratories, Inc. (PA, USA). Pyridine was obtained from EMD Chemicals, Inc. (NJ, USA). Sylon BFT [N, O-bis(trimethylsilyl) trifluoroacetamide (BSTFA): trimethylchlorosilane (TMCS), 99:1] was purchased from Supelco Inc. (PA, USA). 5α-Cholestane (>98%) was obtained from Acros Organics (NJ, USA). All other reagents and chemicals were of analytical grade.

Nanoporous Starch Aerogel (NSA) Production

NSA monoliths were formed from wheat starch under the NSA formation conditions of Example 1. Briefly, NSAs were formed over three main steps, namely, hydrogel formation, solvent exchange, and SC—$CO_2$ drying. Firstly, the hydrogels were produced at a gelatinization temperature of 120° C., starch mass concentration of 10% and mixing rate of 600 rpm for 20 minutes and kept at 4° C. for 48 hours for retrogradation. Then, a five-step solvent exchange took place to obtain alcogels by replacing water with ethanol. Finally, the NSAs were obtained by SC—$CO_2$ drying of the alcogels at 10 MPa, 40° C. for 4 hours. The wheat starch aerogels were characterized and the properties of the NSAs are presented in Table 1. The NSAs were formed in a monolith shape because the monolith shape allowed for determination of the density and shrinkage by measuring the dimensions and weight of the monolith. The porosity was calculated using the following equation:

$$\text{Porosity } (\%) = \left(1 - \frac{\rho_s}{\rho_t}\right) \times 100 \qquad (3)$$

where $\rho_s$ is the bulk density of the aerogel and $\rho t=1.5$ g $cm^{-3}$ is the true density of the starch.

TABLE 1

| The properties of the NSAs | |
|---|---|
| BET surface area | 59.7 ± 0.9 $m^2$ $g^{-1}$ |
| BJH pore size | 19.6 ± 0.4 nm |
| Pore volume | 0.27 ± 0.02 $cm^3$ $g^{-1}$ |
| Density | 0.12 ± 0.00 g $cm^{-3}$ |
| Porosity | 91.9 ± 0.0% |

Impregnation of the Phytosterols into the NSAs

The NSA monoliths were ground and sieved through a 0.85 mm screen (mesh #20) and the powdered NSAs were used for impregnation. Phytosterol impregnation was carried out using a laboratory scale SC—$CO_2$ extraction system (SFT-110, Super-critical Fluids, Inc., DE, USA) in the semi-static mode. The details of the system and its operation have been previously reported.31 The temperatures of the extraction vessel and the restrictor block were set at 70° C. and 95° C., respectively, prior to the experiment. The high pressure vessel was divided into two compartments by glass wool and a sintered filter (0.22 gm). The powder NSA (1.5 g) and phytosterols (0.5 g) were wrapped in a Whatman #41 filter paper (NJ, USA) separately, the phytosterols were placed at the bottom of the vessel and the NSAs were placed at the top of the vessel. The system was pressurized with $CO_2$ at 45 MPa using a high pressure pump and kept at a constant set pressure and temperature for 10 min. $CO_2$ was fed from the bottom of the vessel to first dissolve the phytosterols and then diffuse into the NSA. The $CO_2$ flow rate was adjusted to 1 L $min^{-1}$ (measured at ambient conditions) and maintained constant using a micrometering valve. After 3 hours of impregnation, the system was left to cool to 25° C. naturally and then depressurized to atmospheric pressure at a $CO_2$ flow rate of 1 L $min^-$. Finally, the impregnated NSAs were collected and stored at room temperature (21° C.) until characterization.

Determination of the Impregnation Capacity

The phytosterols impregnated into the NSAs were extracted from 0.2 g of impregnated NSA using 10 mL of chloroform in a glass vial at 50° C. for 1 hour with occasional vortexing. Then, the NSAs were separated from the mixture using Whatman #41 filter paper. The glass vial and filter cake were washed three times with 5 mL of chloroform. The filtrate was analyzed by GC-MS to quantify the total mass of the phytosterol extracted from the NSA. The impregnation capacity was reported as g of phytosterol per g NSA.

Phytosterol Analysis

The phytosterol content and composition were determined using GC-MS. The phytosterol samples were silylated prior to injecting into the GC. Briefly, 1 mL of internal standard (5α-cholestane, 100 μg $mL^{-1}$) was added onto the phytosterol sample. The mixture was dried by blowing nitrogen at room temperature (21° C.). Then, the dry sample was dissolved in 0.5 mL of pyridine and 100 gL of Sylon BFT was added as a silylation agent. This mixture was left in an oven at 50° C. for 30 minutes to complete the silylation reaction. The silylated samples were analyzed using a Hewlett-Packard (HP) 5890 Series II GC interfaced with a HP 5970 MSD quadrupole MS working at 70 eV of ionization voltage. The GC was equipped with a GC column (Rtx-1, 30 m×0.25 mm i.d.; Restek Corporation, PA, USA) and an HP 7673A autosampler. The samples were injected into the GC column at a split ratio of 5:1. Helium was used as the carrier gas. The oven temperature was programmed with an initial hold at 80° C. for 2 minutes, followed by first increase to 210° C. at 15° C. $min^{-1}$, second increase to 250° C. at 5° C. $min^{-1}$, and third increase to 275° C. at 12° C. $min^{-1}$, and then finally maintained at 275° C. for 40 minutes. The injector and detector temperature were both at 280° C. The data was recorded using an HP 59940A MS Chemstation software (HP-UX series). Phytosterol identification was carried out using the NIST/EPA/NIH mass spectral library and build-in library.

Morphology

The morphology of the NSAs was studied using field emission scanning electron microscopy (FE-SEM) (S4700 FE-SEM, Hitachi, Tokyo, Japan). FE-SEM was operated at 5 kV and 15 mA under low vacuum mode. The specimens were mounted on aluminum stubs with double-side conductive carbon tape and then sputter-coated with a chromium layer under vacuum (Desk V HP TSC, Denton Vacuum LLC, NJ, USA). The dimensions of the phytosterols obtained by sudden precipitation of supercritical solutions (SPSS) were determined using ImageJ software (version 1.50i, public domain, National Institutes of Health, USA).

Crystallinity

The crystallinity of the empty and impregnated NSAs, crude phytosterols, SPSS phytosterols, and physical mixture of NSA with SPSS-phytosterols (5 wt %) were determined using an X-ray diffractometer (XRD) (Empyrean, PANalytical B.V., Almelo, Netherlands) equipped with PIXcel$^{3D}$ detector. The system was operated with 1D detection and a Cu Ka beam monochromator at 45 kV and 40 mA. The samples were scanned from 2° to 400 (2Θ) with a step size of 0.05° and an angular scanning velocity of 1.267° $min^-$. The samples were spun throughout the analysis at a rate of 3.75 rpm.

Thermal Analysis

The thermal properties of the NSAs were determined using a differential scanning calorimeter (DSC) (Diamond, Perki-nElmer, Inc., CT, USA). The instrument was calibrated with indium and an empty aluminum pan was used as a reference. The samples (5 mg) were weighed using an electronic balance (ME204E, Mettler Toledo, Ohio, USA) with a precision of 0.0001 g in 50 μL aluminum pans. The samples were heated from 25° C. to 160° C. at a rate of 5° C. $min^{-1}$ under a nitrogen flow of 20 mL $min^{-1}$. The data was analyzed using Pyris Soft-ware Version 8.0 (PerkinElmer, Inc., CT, USA). The crystallinity of SPSS-phytosterols in comparison to crude phytosterols was calculated from the heat of fusion data using the following equation:

$$\text{Crystallinity (\%)} = \frac{\Delta H_{SPSS\text{-}phytosterol}}{\Delta H_{crude\,phytosterol}} \times 100 \qquad (4)$$

where DH is the enthalpy change associated with thermal transition and calculated by integrating the area of the relevant DSC peak.

Fourier-Transform Infrared Spectroscopy

An attenuated total reflectance Fourier-transform infrared spectrometer (ATR-FTIR) (Nicolet 380, Thermo Scientific, MA, USA) was used to examine the functional groups in the empty NSAs and phytosterol impregnated NSAs. FTIR spectra were recorded ranging from 4000 $cm^{-1}$ to 400 $cm^{-1}$ with 128 scans averaged at a spectral resolution of 4 $cm^{-1}$. Nicolet Omnic 8.3 software was used for collecting the data.

Water Solubility of the Phytosterols Impregnated into the NSAs

The water solubility of the phytosterols impregnated into the NSAs was determined according to the method of He et al. (Food Chem., 2016, 192, 557-565) with some modifications. The impregnated NSA (1 g) was mixed with deionized water (100 mL) at 30° C. and 200 rpm for 5 hours. Then, aliquots (10 mL) of the mixture were withdrawn and filtered through Whatman #41 filter paper. The filtrate was transferred into glass vials and dried at 80° C. to obtain the dry phytosterols. Then, the phytosterols were silylated and analyzed by GC.

In Vitro Phytosterol Release

The release of phytosterols from the NSAs was carried out in a 500 mL of simulated gastric fluid (0.1 N HCl, pH=1.2) and intestinal fluid (0.1 M PBS, pH=6.8) based on the recommendation of the U.S. Food and Drug Administration. Impregnated NSAs (1.912 g, corresponding to 100 mg of crude phytosterol based on the impregnation capacity) were placed in a perforated basket (5 μm openings). The release medium was placed in an 800 mL glass beaker and maintained at 37° C. using a hot plate (CIMAREC™, Thermo Scientific, MA, USA). The basket was fixed on the agitator of an overhead stirrer (RW 11, IKA® Works, Inc., NC, USA) and then immersed into the release medium and stirred at 100 rpm. An aliquot of 10 mL was withdrawn and replaced with an equal volume of fresh pre-warmed (37° C.) release medium at pre-determined time intervals (0, 1, 2, 3, 4, 6, 12, 24, and 30 hours). The liquid samples were dried at 80° C. and the residual dry phytosterols were quantified by GC. The release of 100 mg of crude phytosterol was studied under the same conditions and used as a control.

Statistical Analysis

Statistical evaluation of the results was performed using MINITAB® 16.1.1 software (Minitab Inc., State Collage, Pa., USA). Multiple comparison of the means was carried out by Tukey test. Differences were considered to be statistically significant at a 95% confidence interval (p<0.05).

Results and Discussion

Removing water from the gelatinized starch to form a porous starch matrix is critical to obtain starch aerogels. Previous studies have shown that air drying results in the shrinkage and collapse of the porous structure due to high surface tension and capillary forces in the pores. In Example 1, nanoporous aerogels were formed from wheat starch by replacing the water in the starch hydrogel with ethanol and then removing the ethanol via SC—$CO_2$ drying. SC—$CO_2$ drying eliminated the surface tension and the capillary pressure gradient, and thus, preserved the porous structure. In Example 1, the wheat starch aerogel formation parameters (temperature, wheat starch concentration and mixing rate during gelatinization; temperature, pressure, and flow rate of $CO_2$ during SC—$CO_2$ drying) were selected for the highest surface area. Under these conditions, the wheat starch aerogels had outstanding properties: surface area of 59.7 $m^2$ $g^{-1}$, pore size of 19.6 nm, pore volume of 0.27 $cm^3$ $g^{-1}$ and density of 0.12 g $cm^{-3}$ (Table 1).

Figure 10:
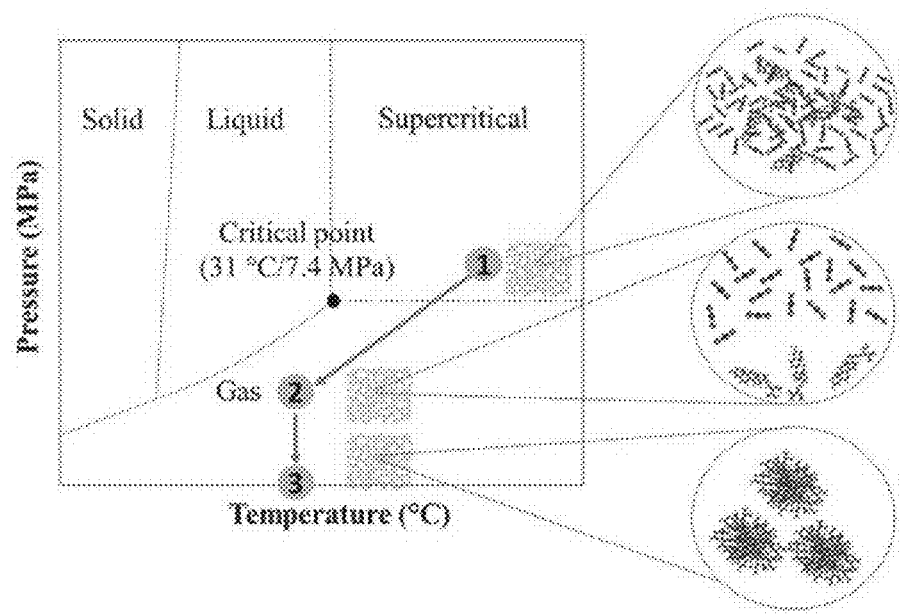
FIG. 10 depicts the mechanism of the size reduction of the phytosterols via impregnation into the NSAs using SC—$CO_2$ as done in Example 2.

Herein, a green approach is used to fabricate phytosterol nanoparticles using NSA in order to enhance the water solubility of the phytosterols. The size and crystallinity of the phytosterols (a standard mixture: 52.8% β-sitosterol, 24.3% stigmasterol, and 22.9% campesterol) were decreased by impregnating them into the NSAs using a controlled SC—$CO_2$ impregnation method. FIG. 9 illustrates the formation of phytosterol nanoparticles via SC—$CO_2$ impregnation into the NSAs. The mechanism behind the SC—$CO_2$ impregnation was first based on controlling the solubility of the phytosterols in the SC—$CO_2$ and then utilization of the nanopores and high surface area of the NSA as a mold to decrease the size and crystallinity by controlling the recrystallization of the phytosterols from the phytosterol-SC—$CO_2$ solvato complex. The impregnation conditions were selected as 45 MPa and 70° C. based on previously reported solubility data of the phytosterols in the SC—$CO_2$. Ciftci et al., Food Chem., 2012, 60, 12482-12490. As shown in FIG. 10, the phytosterols were first dissolved in SC—$CO_2$ and then, the phytosterol-SC—$CO_2$ solvato complex was diffused into the NSA. Then, the state of the $CO_2$ was changed from its supercritical phase to the gas phase by decreasing the temperature below the critical temperature of $CO_2$ (31° C.), which automatically decreased the pressure. Upon changing the state of the $CO_2$, the solubility of the phytosterols in the $CO_2$ decreased to zero. Then, the phytosterols that formed a solvato complex with SC—$CO_2$ precipitated in the nanopores due to the sudden decrease in their solubility, described as "sudden precipitation of super-critical solutions (SPSS)".

The nanopores of the NSA act as a mold and prevent the formation of bigger and relatively well-ordered phytosterol crystals during recrystallization due to the short time of crystallization.

Figures 11A, 11B, 11C, 11D, 11E, 11F, 11G, 11H:
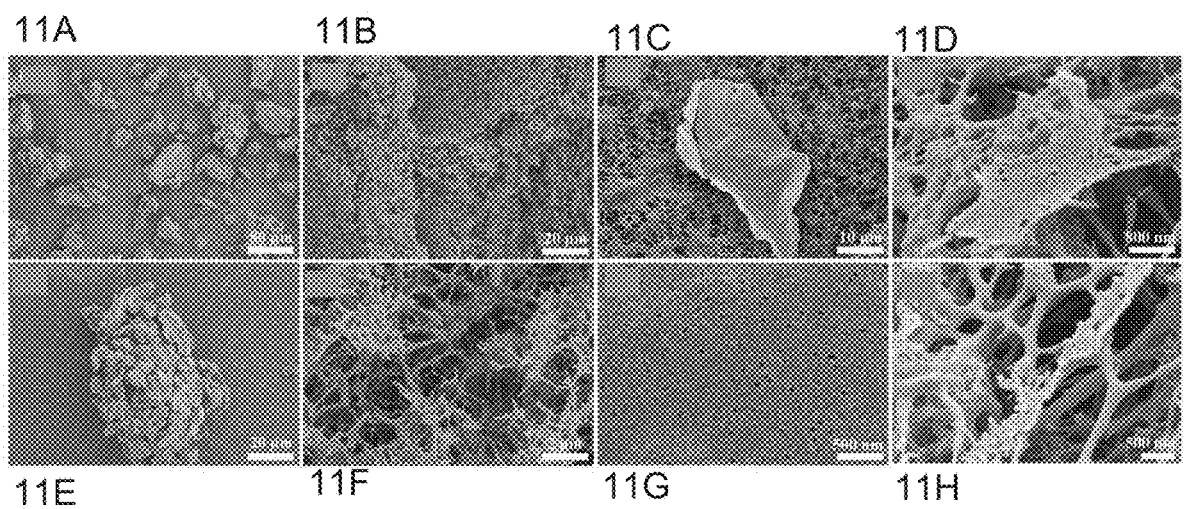
FIGS. 11A-11H depict low and high magnification SEM micrographs of the crude phytosterols (FIGS. 11A & 11E), empty wheat starch aerogels (FIGS. 11B & 11F) and phytosterol impregnated aerogels (FIGS. 11C, 11D, 11G and 11H).

FIGS. 11A-11H presents the SEM images of the crude phytosterols (FIGS. 11A & 11E), the empty NSA (FIGS. 11B & 11F) and phytosterols impregnated into the NSA (FIGS. 11C, 11D, 11G and 11H). The size of the crude phytosterol crystals varied from 20 μm to 115 μm (FIG. 11A). The high surface area of NSA allowed the formation of a high surface area thin film of phytosterol that was formed of spherical phytosterol nanoparticles (FIG. 11C). The high magnification of the phytosterol film revealed that the phytosterol film was formed by agglomeration of spherical phytosterol nanoparticles (FIG. 11D). Isolated nanoparticles and a net-like structure formed of phytosterol nanoparticles were also obtained (FIGS. 11G & 11H). The morphology of the impregnated phytosterols depends on the recrystallization mechanism, which was affected by the cooling rate.

SC—$CO_2$ impregnation did not have any negative effect on the nanoporous structure of the NSA with the three-dimensional open porous network structure being preserved after impregnation. The specific phytosterol impregnation (adsorbed phytosterol per specific aerogel surface area) was $9.23 \times 10^{-4} \pm 1.00 \times 10^{-5}$ g $m^2$. The phytosterol impregnation capacity was 0.055±0.001 g phytosterol per g NSA.

There are a few reported studies using SC—$CO_2$ to decrease the size of phytosterols. Turk and Lietzow (AAPS PharmSciTech, 2004, 5, e56) obtained agglomerates of submicron phytosterol particles via a rapid expansion of supercritical solutions (RESS) process, where a supercritical phytosterol and $CO_2$ mixture was expanded into an aqueous surfactant solution, which generated an aqueous solution containing submicron phytosterol particles. Recently, plate-like phytosterol crystals with thicknesses ranging between 150 nm and 450 nm were obtained using the depressurization of an expanded liquid organic solution (DELOS) process in an effort to decrease the size of the phytosterols. Moreno-Calvo et al., Cryst. Growth Des., 2014, 14, 58-68. However, the crystallinity of the phytosterols processed by DELOS was increased up to 108%, which may have negative effect on the solubilization rate. Moreover, the DELOS process uses organic solvents, which renders it as a non-green process. In another study, which did not use supercritical fluids, rod-like colloidal phytosterol particles were formed from ethanol via anti-solvent precipitation in water, where the particles had an average particle length in the range of 500-700 nm and particle diameters between 80 and 250 nm. Rossi et al., Soft Matter, 2010, 6, 928.

Figure 12:
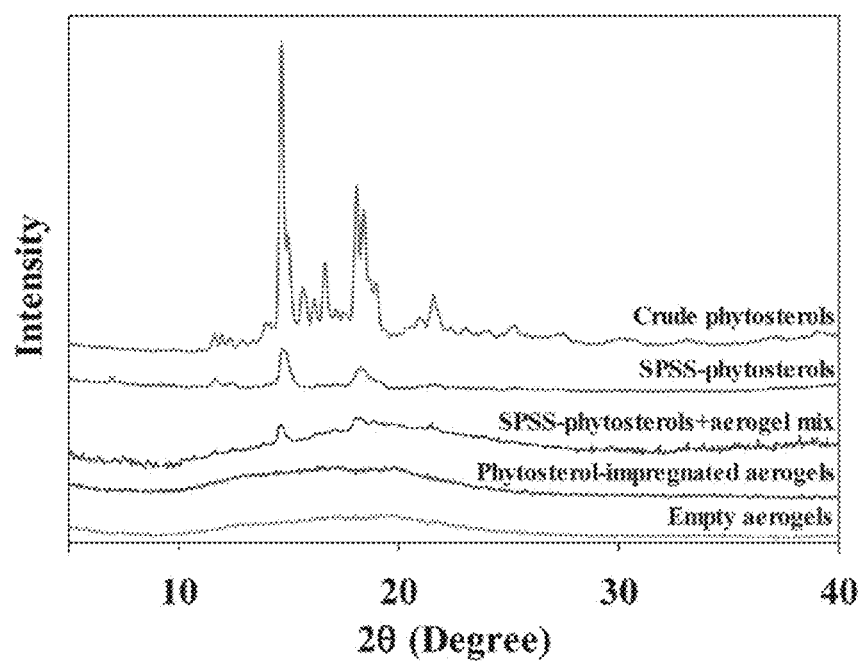
FIG. 12 depicts the XRD patterns of the crude phytosterols, SPSS-phytosterols, a physical mixture of NSA with SPSS-phytosterols (5 wt %), NSAs impregnated with phytosterols and empty NSAs.

XRD patterns showing the crystallinity of the crude phytosterols, SPSS-phytosterols, empty NSA, and NSA impregnated with phytosterols are depicted in FIG. 12. SPSS-phytosterols were obtained via precipitation of the phytosterol-SC—$CO_2$ solvato complex at 70° C. and 45 MPa in order to mimic the impregnated phytosterols as it was not possible to isolate them from the NSA. The XRD pattern of empty NSAs did not have any sharp peaks, indicating an amorphous structure. Crude phytosterol had strong characteristic peaks at $2\Theta$=14.60, 15.6°, 16.2°, 16.7°, 18.2°, 21.6°, and 25.1°, respectively. These sharp peaks indicate the crystalline part of the crude phytosterols. The characteristic peaks of the crude phytosterols were not observed in the phytosterol impregnated NSAs, which indicated that the impregnated phytosterols were in a more amorphous form. The SPSS-phytosterols had characteristic peaks at $2\Theta$=11.60, 14.6°, and 18.2°, respectively. The intensity of these peaks was much lower than that of crude phytosterols, which indicates that the crystallinity of crude phytosterols was decreased by SC—CO2 impregnation. This was also justified by the XRD pattern of the physical mixture of NSA with SPSS-phytosterol (5 wt %) where the same characteristic peaks were observed at $2\Theta$=14.60 and 18.2°, respectively. The SPSS-phytosterols had longer (50 mm) and thicker (500 nm) particles (measured from the SEM images; data not shown) compared to those of the impregnated-phytosterols observed from the SEM images. Therefore, it is expected that the phytosterols impregnated into the NSA were less crystalline. The degree of crystallinity of the SPSS-phytosterols was calculated to be 88.4% with respect to crude phytosterols by the enthalpy change associated with thermal transition, which is in agreement with the XRD data. The NSA matrix eliminated the sensitivity required to get a clear melting peak; therefore, the SPSS-phytosterols were used for the crystallinity calculations.

Figure 13:
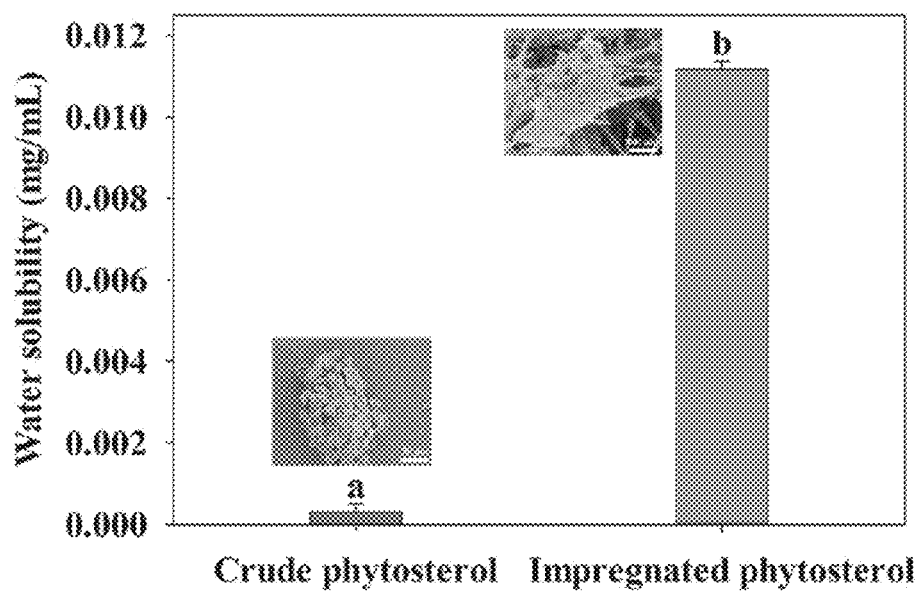
FIG. 13 depicts the water solubility of the crude phytosterols and the phytosterols impregnated into the NSAs at 30° C. after 5 hours. Different lowercase letters over the error bar denote significant differences ($p<0.05$).
Figures 14A, 14B:
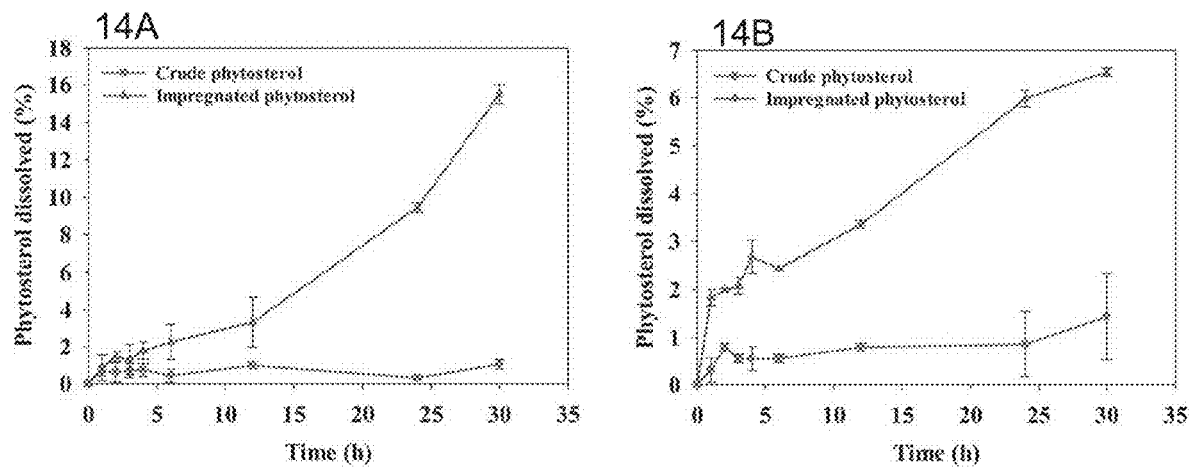
FIGS. 14A & 14B depict the dissolution profiles of the phytosterols impregnated into the NSAs in simulated (FIG. 14A) gastric and (FIG. 14B) intestinal fluids.

Impregnation of the phytosterols into the NSAs increased the water solubility (dispersibility) of the phytosterols significantly ($p<0.05$) (FIG. 13). The water solubility of the crude phytosterols was $0.0003\pm0.0002$ mg mL$^{-1}$, whereas it was $0.0112\pm0.0002$ mg mL$^{-1}$ for the impregnated-phytosterols. Water solubility is an important parameter limiting the bioavailability of many lipophilic bioactives. Difficulty in dislocating the molecules from the crystal and difficulty in solvating the dislocated molecules are two important factors decreasing the solubility. In this method, the phytosterol molecules are separated from the crystal by forming a phytosterol-SC—$CO_2$ solvato complex and then, the dissolved molecules form nanosize phytosterol particles that can be dispersed in water. The solubility of a solute in a solvent depends on the forces of attraction between the solute and solvent molecules. If these forces overcome the forces holding the solid intact and solvent aggregates together, then the solid can be dissolved into the solvent. The lattice free energy of the solids has a critical effect on these forces where a higher free energy results in an increase in the solubility. Therefore, as expected, having a more amorphous structure, which has higher free energy compared to its crystalline form contributed to the enhanced solubility of the phytosterols in water. The release rate and water solubility are crucial factors determining the bioavailability of the lipophilic bioactives. The crystalline structure of the phytosterols results in very low bioaccessibility due to inefficient absorption in the intestine. It has been reported that the in vitro bioaccessibility experiments of colloidal phytosterols show an improvement in solubility in dietary mixed micelles, which reduced the micellar cholesterol concentration by 47%. Mel'nikov et al. (Chem. Phys. Lipids, 2004, 127, 121-141) reported similar results in which the intestinal uptake of cholesterol was reduced by plant sterols. The absorption of phytosterols is very low (<2%) compared to cholesterol (up to 60%). The main criterion to increase phytosterols absorption is to solubilize them in the intestinal mixed micelles to reach the site of absorption. Therefore, the solubility and release rate of phytosterols are highly associated with bioaccessibility and, consequently, the bioavailability. FIGS. 14A & 14B presents the dissolution (release) of the phytosterols impregnated in the NSAs in the simulated gastric (FIG. 14A) and intestinal fluid (FIG. 14B). The dissolution pattern of the phytosterols from the NSAs followed a concave-upward profile and the dissolution rate was significantly improved in simulated gastric fluid. The cumulative dissolution of the phytosterols from NSAs was 15.5%±0.5% after 30 hours and it was significantly higher than that of the crude phytosterols (1.0%±0.3%) ($p<0.05$). Correspondingly, the maximal concentration of the phytosterols in the simulated gastric fluid was 15 times higher than that of the crude phytosterols. The cumulative phytosterols dissolved from NSAs increased with a constant rate up to 6.53%±0.09%. The phytosterol release mechanism mainly depends on the carrier, impregnated compound, and the interaction between the compound and the carrier. The nanosize and more amorphous structure of the impregnated phytosterols improved the release and water solubility, however their release from the NSA matrix is also important to enhance the bioaccessibility and, in turn, the bioavailability. Starch aerogels are hydrophilic and consequently, the water uptake and collapse of the aerogel network are effective in the release properties. Therefore, both diffusion and erosion were important during the release of the impregnated phytosterols. The highest release was obtained in an acidic medium (gastric fluid) (15.5%±0.5%) and was higher than the release in a neutral medium (intestinal fluid) (6.53%±0.09%) due to the acidic hydrolysis of the NSA matrix. Moreover, starch has a higher solubility at acidic pH than that found at a neutral pH, which resulted in the faster release of the phytosterol nanoparticles from the NSA.

Figure 15:
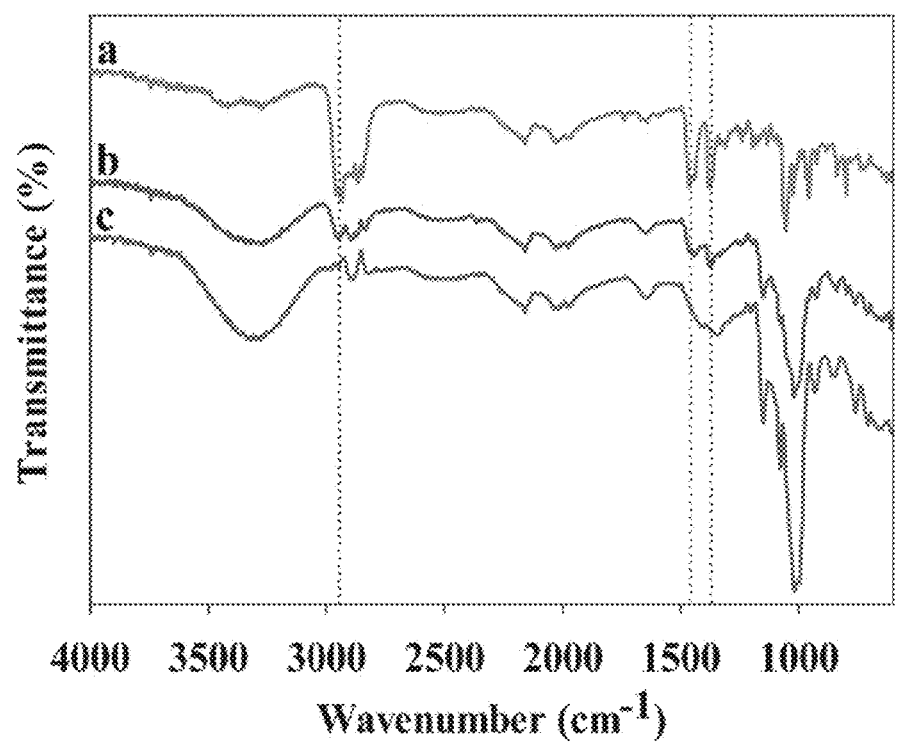
FIG. 15 depicts the Attenuated Total Reflection Fourier Transform Infrared spectroscopy (ATR-FTIR) spectra of the (line "a") crude phytosterols, (line "b") phytosterol-impregnated NSA and (line "c") empty NSA.

The ATR-FTIR results show that there were no interactions between the NSA matrix and the impregnated phytosterols (FIG. 15). The crude phytosterols (FIG. 15, line "a") exhibited characteristic bands between 2980 and 2810 cm$^{-1}$ for the asymmetric stretching vibrations of the C—H bonds in $CH_2$ and $CH_3$ groups, between 1480 and 1400 cm$^{-1}$ for the C—H bending vibrations, between 1390 and 1350 cm$^{-1}$ for the interactions of O—H bending and C—O stretching in the C—O—H group and between 1060 and 1025 cm$^{-1}$ for the secondary C—O vibrations in the C—O—H group. Some characteristic peaks of the crude phytosterols were also observed in the phytosterol impregnated NSAs (FIG. 15, line "b"). The spectrum obtained for the starch aerogels (FIG. 15, line "c") showed a broad peak in the range of 3580-3030 $cm^{-1}$ for the O—H stretching and peaks at 2880 $cm^{-1}$ for $CH_2$ stretching vibrations, 1153 $cm^{-1}$ for C—O—C glucosidic bridging, 1181 $cm^{-1}$ for C—C stretching vibrations and 1025 $cm^{-1}$ for C—O stretching vibrations. Although, a previous report discussed the possibility of binding between the hydroxyl groups on the surface of the phytosterols and the carbonyl groups on starch (Liu et al., J. Pharm. Biomed. Anal., 2016, 118,267-275), any interactions between the phytosterols and NSA matrix were not identified based on no shifts being observed for the characteristic peak positions. The decrease in the intensity of the peak attributed to O—H stretching (3580-3030 $cm^{-1}$) after impregnation could be a result of the phytosterols, which do not have an intense O—H stretching peak. Phytosterols tend to have interactions with each other rather than with the NSA matrix, as seen from the SEM images (FIG. 11C). Having no chemical bonding with the NSA matrix also contributes to the enhanced release of the phytosterol particles from the NSA. However, there was a slower release in the first 6 hours in both simulated gastric and intestinal fluid, which could be explained by the incomplete degradation of the starch aerogel matrix or mass transfer limitations due to swollen starch. The following sharp increase in the release from the NSA could be due to having more effective diffusion and convective mass transfer after erosion of the NSA matrix.

Based on the results, in the longer-term, NSAs and the $SC-CO_2$ impregnation process can improve the health benefits of the water-insoluble bioactives, enable food manufacturers to add water-insoluble bioactives into both low- and high-fat foods and beverages to produce health-promoting foods in a clean and simple manner, and maximize the utilization of the bioactives derived from agricultural products. This approach will reduce bioactive waste and the water and energy consumption used to produce bioactives. This would be a significant advance, particularly because the proposed method is green, does not use toxic chemicals and produces no environmental pollution. Further, the dry formulation will make the handling, storage and transportation more convenient.

Example 3

In this Example, the bioaccessibility of phytosterols using nanoporous starch bioaerogels was determined.

Materials and Methods

Wheat starch (~25% amylose) was kindly provided by Manildra Milling Corporation (IA, USA). High amylose corn starch (Hylon VII, ~70% amylose) was obtained from Ingredion (NJ, USA). Carbon dioxide (99.99% purity) was purchased from Matheson Tri-Gas, Inc. (PA, USA), and ethanol (100%) was supplied by Decon Laboratories, Inc. (PA, USA). Crude phytosterols originated from soybeans in the free form were purchased from MP Biomedicals (OH, USA). Crude phytosterols were analyzed by gas chromatography-mass spectrometry (GC-MS) using the method of Ubeyitogullari and Ciftci and its composition was found to be 51.6±0.1% β-sitosterol, 23.8±0.1% stigmasterol, and 24.6±0.1% campesterol. Sylon BFT [N, O-bis(trimethylsilyl)trifluoroacetamide (BSTFA):trimethylchlorosilane (TMCS), 99:1] was purchased from Supelco Inc. (PA, USA). Pyridine was obtained from EMD Chemicals, Inc. (NJ, USA) and 5α-cholestane (>98%) was purchased from Acros Organics (NJ, USA). Lipase A "Amano" 12 lipase A12 (from fungus *Aspergillus niger*, 132,000 U/g) was generously provided by Amano Enzyme Inc. (IL, USA). α-Amylase from *Bacillus subtilis* was purchased from MP Biomedicals (OH, USA). Pepsin from porcine gastric mucosa, pancreatin from porcine pancreas, lipase from porcine pancreas, bile extract from porcine were all obtained from Sigma-Aldrich (MO, USA). All other chemicals were of analytical grade.

Preparation of Nanoporous Starch Aerogels (NSAs)

NSAs were formed from wheat and corn starches. Briefly, starch dispersions (10 wt. %) were first gelatinized at 120° C. for 20 min with a mixing rate of 600 rpm in a high pressure reactor (4520 Bench Top Reactor, Parr Instrument Company, IL, USA) to obtain a hydrogel. The hydrogels were kept at 4° C. for 48 h for retrogradation. Then, the water in the hydrogels was replaced with ethanol to obtain an alcogel using a solvent exchange step. Solvent exchange was carried out by soaking hydrogel monoliths in 30, 50, 70, and 100% (v/v) ethanol for 1 h residence time, and 100% ethanol for 24 h. Finally, alcogels were dried using $SC-CO_2$ at 40° C., 10 MPa for 4 h with a $CO_2$ flow rate of 0.5 L/min to obtain aerogels. Aerogels were characterized for their surface area and pore size. Properties of the developed aerogels are presented in Table 2.

TABLE 2

| The textural properties of the NSAs. | | |
|---|---|---|
| | Wheat starch aerogel | Corn starch aerogel |
| BET surface area ($m^2/g$) | 61.5 ± 1.5 | 220.5 ± 5.2 |
| BJH pore size (nm) | 19.0 ± 1.3 | 7.4 ± 0.1 |
| Pore volume ($cm^3/g$) | 0.27 ± 0.01 | 0.36 ± 0.01 |
| Density ($g/cm^3$) | 0.11 ± 0.01 | 0.16 ± 0.01 |
| Porosity (%) | 92.5 ± 0.3 | 89.4 ± 0.2 |

Impregnation of the Phytosterols into the Aerogels

Corn starch aerogel monoliths (CSA-M) and wheat starch aerogel monoliths (WSA-M) were ground and sieved through 0.85 mm screen (mesh #20) to obtain the powder forms. CSA-M, corn starch aerogel powder (CSA-P), WSA-M and wheat starch aerogel powder (WSA-P) were impregnated with phytosterols. $SC-CO_2$ impregnation was carried out to maximize impregnation capacity. Aerogels (1 g) and crude phytosterols (0.5 g) were separately wrapped in a Whatman #1 filter paper (NJ, USA) and placed at the top and bottom compartments of the high pressure vessel, respectively. The details of the $SC-CO_2$ impregnation system according to Ubeyitogullari and Ciftci (J. Food Eng. 2017, 207, 99-107). The system was pressurized to 45 MPa with $CO_2$ using a double head high pressure syringe pump (Model 260D, Teledyne Isco Inc., NE, USA). The vessel temperature was kept constant at 90° C. during impregnation. Semi-dynamic $SC-CO_2$ impregnation was carried out by opening the exit valve every 10 min adjusting the flow rate of $CO_2$ to 1 L/min (measured at ambient conditions) for 1 min. After 1 h of impregnation, the system was cooled down to 25° C. by blowing $CO_2$ from a compressed $CO_2$ cylinder (6 MPa) where a cooling rate of 10° C./min was achieved. In order to improve the impregnation capacity, three successive impregnation cycles were carried out with fast cooling. Then, the system was depressurized to atmospheric pressure with a $CO_2$ flow rate of 1 L/min (measured at ambient conditions). Lastly, phytosterol impregnated aerogels were collected from the vessel and kept at room temperature (21° C.) until characterized.

Determination of the Impregnation Capacity

Impregnation capacity of the aerogel samples was determined by quantification of the phytosterols extracted from approximately 0.15 g of impregnated aerogels. Prior to the extraction, 50 µL of 5α-cholestane (2.25 mg/mL) was added as internal standard. The extraction was carried out by 5 mL of chloroform at 50° C. for 1 h with occasional vortexing. Then, the dispersion was filtered through a 0.45 µm pore-size filter (WHATMAN™, Buckinghamshire, UK) and washed three times with 3 mL of chloroform. The filtrate was evaporated to dryness under a stream of nitrogen at room temperature (21° C.) using a Reacti-Vap evaporation unit (Model TS-18825, ThermoFisher Scientific, PA, USA). Phytosterols in the dry residue were silylated and quantified by GC as described below (see Phytosterol analysis). The impregnation capacity was reported as mg phytosterols/g aerogel. All experiments were conducted in triplicates.

Phytosterol Analysis

Phytosterol content of the samples (aerogels and bioaccessible fractions) was determined by a Hewlett-Packard (HP) 6890 GC equipped with a flame ionization detector (FID). The samples were derivatized according to Ubeyitogullari and Ciftci (J. Food Eng. 2017, 207, 99-107). Briefly, dry residues were dissolved in 0.3 mL of pyridine and silylated with 1 mL of Sylon BFT at 50° C. for 30 min. An aliquot of 1 µL of derivatized sterols was injected onto a capillary column (DB-35MS, 25×0.20 mm×0.33 µm; J&W, Agilent Technologies, CA, USA). The injection was performed in a splitless mode with an HP G1512A autosampler. The flow rate of helium (carrier gas) was 0.5 mL/min. The temperature of the injector and detector were set to 270 and 300° C., respectively. The column temperature was programmed with an initial hold at 100° C. for 5 min, followed by a first ramp to 250° C. at 25° C./min and held for 1 min at 250° C., and a final ramp to 290° C. at 3° C./min and kept at 290° C. for 40 min.

Morphology

Morphology of the samples was analyzed by a field emission scanning electron microscope (S4700 FE-SEM, Hitachi, Tokyo, Japan). Operating conditions were 5 kV and 15 mA under low vacuum. The specimens were placed on double-side conductive carbon tape mounted on the aluminum stubs and sputter-coated with chromium (Desk V HP TSC, Denton Vacuum LLC, NJ, USA). Particle size determination was carried out using ImageJ v. 1.50i software (public domain, National Institutes of Health, USA) from the SEM images. Phytosterol particle size was calculated from randomly selected 50 particles and reported as mean±standard deviation.

Crystallinity

Crystallinity of the samples was determined using an X-ray diffractometer (XRD) (Empyrean, PANalytical B.V., Almelo, Netherlands) equipped with a PIXcel$^{3D}$ detector operated at 1D detection. The XRD was operated at 45 kV and 40 mA. Aerogel monoliths were ground and sieved through 0.85 mm screen (mesh #20) prior to analysis. The samples were scanned between 2° and 40° (2θ) with a step angle of 0.05° at a scan rate of 0.927°/min. The samples were spun at 3.75 rpm throughout the analysis.

Simulated Digestion

A sequential oral, gastric, and intestinal digestion was performed according to the method of Minekus et al. (Food & Function. 2014, 5, 1113-1124). Simulated digestion fluids (simulated salivary fluid (SSF), simulated gastric fluid (SGF) and simulated intestinal fluid (SIF)) were prepared according to Minekus et al. (Food & Function. 2014, 5, 1113-1124). All the enzyme units were calculated according to the activity of the enzymes declared by the manufacturers. Simulated digestion experiments were performed in triplicate. The physical mixture of crude phytosterols with the empty aerogels at the same impregnation capacity was used as a control.

Simulated Oral Digestion

Oral phase digestion was conducted according to Minekus et al. (Food & Function. 2014, 5, 1113-1124) with some modifications based on Mennah-Govela and Bornhorst (J. Food Eng. 2016, 191, 48-57). Briefly, 3.5 mL of SSF electrolyte stock solution was added into a 50 mL-Erlenmeyer flask. Then, the sample (0.25 g) and α-amylase solution (0.5 mL, 750 U/mL) were included into the flask to obtain an α-amylase concentration of 75 U/mL of in the final mixture. Next, 0.975 mL of deionized water and 25 µL of 0.3 M CaCl$_2$ were added and the pH of the mixture was adjusted to 7.0. Finally, the mixture was incubated at 37° C. and 150 rpm in a shaking water bath (Precision SWB 27, Thermo Fisher Scientific, NH, USA) for 30 seconds.

Simulated Gastric Digestion

Following the oral digestion, 3.25 mL of SGF electrolyte stock solution (pH 3.0) was added into the flask and the pH was adjusted to 3.0 using 75 µL of 1 M HCl solution. Then, porcine pepsin (0.5 mL, 40 000 U/mL) and fungal lipase (as an analogue to human gastric lipase, 0.25 mL, 1000 U/mL) solutions were included. Afterwards, 0.3 M CaCl$_2$ solution (2.5 µL) and deionized water (0.923 mL) were added. Therefore, the final ratio of oral bolus to SGF of 50:50 (v/v) was achieved. Finally, the mixture was placed in the shaking water bath at 37° C. and 100 rpm for 2 h. The pH was monitored throughout the gastric digestion and kept at pH 3.0 using 1 M HCl solution.

Simulated Intestinal Digestion

Gastric chyme (10 mL) obtained after gastric digestion was mixed with 6.125 mL of SIF electrolyte stock solution. The amount of pancreatin was determined according to the α-amylase activity aiming to achieve a final α-amylase activity of 200 U/mL and therefore 1.25 mL of pancreatin solution with α-amylase activity of 3200 U/mL was prepared. Extra porcine pancreatic lipase (3310 U) was included into the pancreatin solution to have a final lipase activity of 2000 U/mL in the final mixture. Subsequently, 0.625 mL of 320 mM fresh bile solution (made in SIF), 1.95 mL of deionized water and 20 µL of 0.3 M CaCl$_2$ were added into the flask. The pH was adjusted to pH 7.0 using 30 µL of 1 M HCl solution. Therefore, the final ratio of gastric chyme to SIF of 50:50 (v/v) was obtained. Finally, the mixture was incubated in the shaking water bath at 37° C. and 100 rpm for 2 h. The pH of the mixture was monitored and re-adjusted to pH 7.0 using 1 M HCl solution during the intestinal digestion.

Obtaining the Bioaccessible Fraction after Simulated Digestion

The bioaccessible fraction (supernatant) was obtained by centrifugation of the digested samples at 4000 rpm and 4° C. for 90 min (Allegra X-15R, Beckman Coulter, CA, USA) [35]. The bioaccessibility (%) of the phytosterols was calculated using the following equation:

$$\text{Bioaccessibility (\%)} = \frac{\text{Phytosterols in the bioaccessible fraction}}{\text{Total phytosterols included}} * 100 \quad (5)$$

The concentration of phytosterols in the bioaccessible fraction was determined using a GC as described in the Phytosterol analysis after saponifying the samples prior to silylation. Briefly, 50 μL of 5α-cholestane (2.25 mg/mL) was added onto 4 mL of bioaccessible fraction. Afterwards, the mixture was saponified with 4 mL of 1 N KOH in methanol at 40° C. for 1 h and kept at room temperature for 18 h. Next, 2 mL of deionized water was added to the mixture and vortexed for 10 seconds. Then, the unsaponifiable fraction was extracted with hexane/methyl tert-butyl ether mixture (50:50, v/v) and the extract was dried under a stream of nitrogen at room temperature. Finally, the dry residues were silylated and analyzed as described in the Phytosterol analysis.

Hydrolysis of the starch aerogels during digestion. The reducing sugar content of the bioaccessible fractions was determined using the 3,5-dinitrosalicylic acid (DNS) method (described in Miller, Anal. Chem. 1959, 31, 426-428). The absorbance was read at 540 nm with a UV/VIS spectrophotometer (Evolution 201, Thermo Scientific, USA). An external calibration curve prepared with glucose was used to calculate the number of moles of reducing sugars. Starch aerogel hydrolysis (%) during simulated digestion was determined as follows:

$$\text{Aerogel hydrolysis (\%)} = \frac{\text{Moles of reducing sugars in the bioaccessible fraction}}{\left(\frac{\text{weight of starch}}{162}\right)} * 100 \quad (6)$$

Statistical Analysis

Data was reported as the mean±standard deviation. The analysis of variance (ANOVA) with Tukey's multiple comparison test was performed to evaluate the differences among various treatments. Differences were considered significant when $p<0.05$. All statistical analysis was carried out using Minitab 16.1.1 software (Minitab Inc., State Collage, Pa., USA).

Results and Discussion

Aerogel Formation

As described herein, solvent exchange was carried out to replace the water in the hydrogel with ethanol, which has higher solubility in $SC-CO_2$. The drying step preserved the porous structure of the gel. Without being bound by theory, $SC-CO_2$ drying has the capability of eliminating the capillary forces during drying to produce high surface area aerogels, which cannot be achieved by conventional drying techniques.

The properties of the starch aerogels are presented in Table 2. WSAs had a surface area of 62 m²/g with a pore size of 19 nm. The density and porosity of WSAs were 0.11 g/cm³ and 93%, respectively. However, corn starch produced a higher surface area (220 m²/g) aerogel compared to WSA. This difference was due to the amylose:amylopectin ratio of the starches. Amylose fraction of the starch was responsible for the mesoporosity of the aerogels and therefore higher surface area was obtained with corn starch, which had higher amylose content. CSAs had a smaller pore size (7.4 nm) but a higher density (0.16 g/cm³) compared to WSAs (Table 2). Porosities of the aerogels were similar and were calculated using the true density of 1.5 g/cm³.

Formation of Phytosterol Nanoparticles Using the Nanoporous Starch Aerogels

Phytosterol nanoparticles were generated by $SC-CO_2$ impregnation of phytosterols into nanoporous starch aerogels using the impregnation conditions. First, phytosterols were dissolved in $SC-CO_2$ to form a phytosterol-$SC-CO_2$ solvato complex. Then, the pores of the aerogels were filled by this complex by diffusion into the pores. The system was quickly cooled down (10° C./min), which decreased the solubility of phytosterols in $SC-CO_2$, as $CO_2$ was not supercritical anymore. Consequently, phytosterol molecules recrystallized in the nanopores of the aerogels. During recrystallization, nanopores acted as a mold and physical barrier to prevent formation of large phytosterol crystals. Finally, the system was depressurized to atmospheric pressure at 25° C. where $CO_2$ is liquid. Depressurization from liquid $CO_2$ prevented the extraction of phytosterol nanoparticles from the aerogels due to very low solubility of phytosterols in liquid $CO_2$ (<0.3 mg sitosterol/g $CO_2$).

Figure 16:
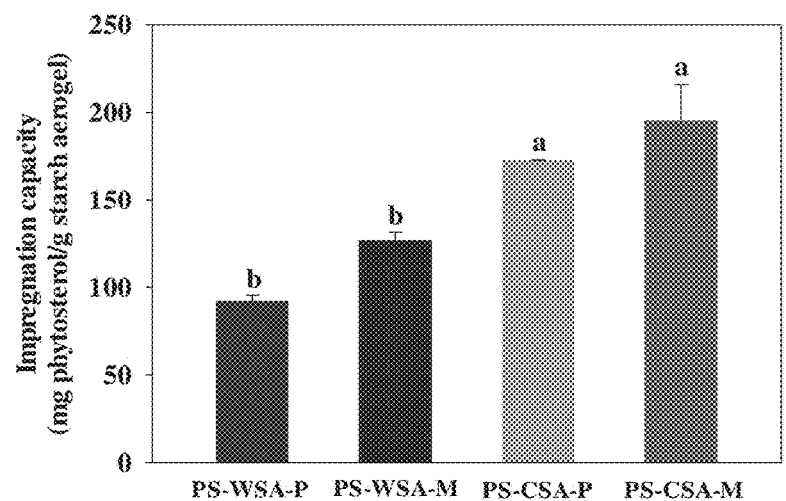
FIG. 16 depicts phytosterol impregnation capacities of the wheat and corn starch aerogels.

Phytosterols were impregnated into the monolithic (PS-WSA-M and PS-CSA-M) and powdered (PS-WSA-P and PS-CSA-P) aerogels. Higher impregnation capacities were obtained by CSA compared to WSA in either monolith or powdered form (FIG. 16) ($p<0.05$). The highest impregnation capacity (195 mg phytosterols/g CSA) was obtained with PS-CSA-M but it was not significantly different than the impregnation capacity of PS-CSA-P (173 mg phytosterols/g CSA) ($p>0.05$). Use of PS-WSA-M resulted in a similar impregnation capacity (126 mg phytosterols/g WSA). As presented herein, the impregnation capacity was improved with CSA, which had higher surface area and pore volume. The aerogel shape (monolith or powder) used for impregnation did not have a significant effect on the impregnation capacity ($p>0.05$) (FIG. 16).

Morphology

Figures 17A, 17B, 17C, 17D, 17E, 17F, 17G, 17H:
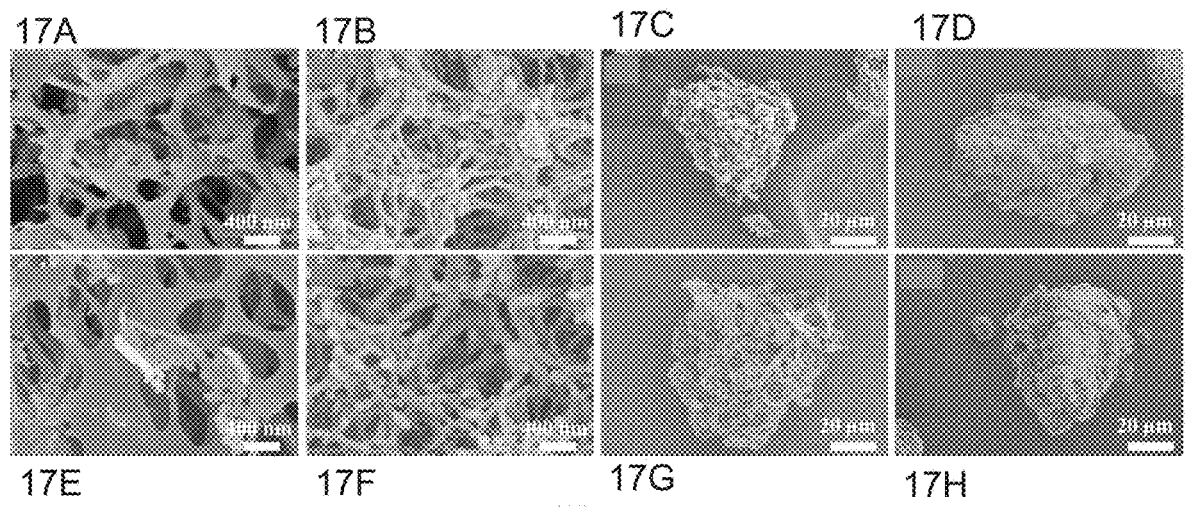
FIGS. 17A-17H depict SEM micrographs of (FIG. 17A) empty WSA-M, (FIG. 17) PS-WSA-M, (FIG. 17B) empty CSA-M, (FIG. 17F) PS-CSA-M, (FIG. 17C) empty WSA-P, (FIG. 17G) PS-WSA-P, (FIG. 17D) empty CSA-P and (FIG. 17H) PS-CSA-P.

Even though the aerogel shape did not affect the impregnation capacity significantly, it affected the morphology of the impregnated phytosterols. FIGS. 17A-17H depict SEM images of the empty (FIGS. 17A-17D) and phytosterol-impregnated (FIGS. 17E-17H) aerogels. Both empty WSA-M and CSA-M had an open porous network structure (FIGS. 17A & 17B). However, the aerogels prepared with high amylose corn starch showed a more homogenous fine fibrillar structure. The gap between the openings was smaller in CSA than in WSA and resulted in higher density aerogels with cornstarch (Table 2). The thickness of the fibrils were about 130 and about 55 nm for WSA and CSA, respectively. Grinding the aerogel monoliths did not affect the porous structure of the aerogels (FIGS. 17C & 17D). The size of the WSA-P (FIG. 17C) and CSA-P (FIG. 17D) particles were about 60 and about 70 μm, respectively. The nanoporous structure of the aerogels was not affected by the $SC-CO_2$ impregnation process. PS-WSA-M generated spherical phytosterol nanoparticles with an average particle size of 70 nm (FIG. 17E); however, phytosterol particles in the PS-CSA-M were not visible under SEM. The fibrils of the CSA were thicker after impregnation with phytosterols (FIG. 17F) because phytosterols formed a nanoscale layer on the CSA matrix. On the other hand, impregnation into powdered aerogels resulted in thin plate-like phytosterol crystals (thickness less than 200 nm) in the aerogel matrix (FIGS. 17G & 17H). During the recrystallization step of $SC-CO_2$ impregnation into WSA-P and CSA-P, phytosterol particles had a higher chance to interact and form a well-ordered structure because of a higher tendency to form aggregates rather than being isolated. The larger void space between the aerogel powders compared to the gap between the openings of the aerogel monoliths favored crystal growth. However, the monolithic shape of the CSA and WSA acted as a mold and prevented the formation of large phytosterol crystals due to the limited amount of phytosterols in the nanopores of the aerogels.

$SC-CO_2$ has been utilized in other techniques including DELOS, RESS, and RESSAS to generate phytosterol particles. The DELOS process produces plate-like phytosterol crystals with a particle size less than 6.5 μm and a thickness varying between 150 and 450 nm. On the other hand, the RESS process generates smaller phytosterol particles (ranging between 166-219 nm) but they form aggregates. RESSAS, in which expansion takes place in an aqueous surfactant solution instead of air, produces submicron phytosterol agglomerates. Expanding into Tween 80 solution results in formation of phytosterol particles with a particle size of 270 nm. When 0.22 or 1.1 wt. % sodium dodecyl sulphate (SDS) solution is used, the particle size decreases to 50 nm; however, agglomerated particles are formed. The difficulty in controlling the particle size and the use of organic solvents to generate liquid formulation with surfactants makes the applications of the above-mentioned $SC-CO_2$-based methods in the food industry challenging.

Figure 18:
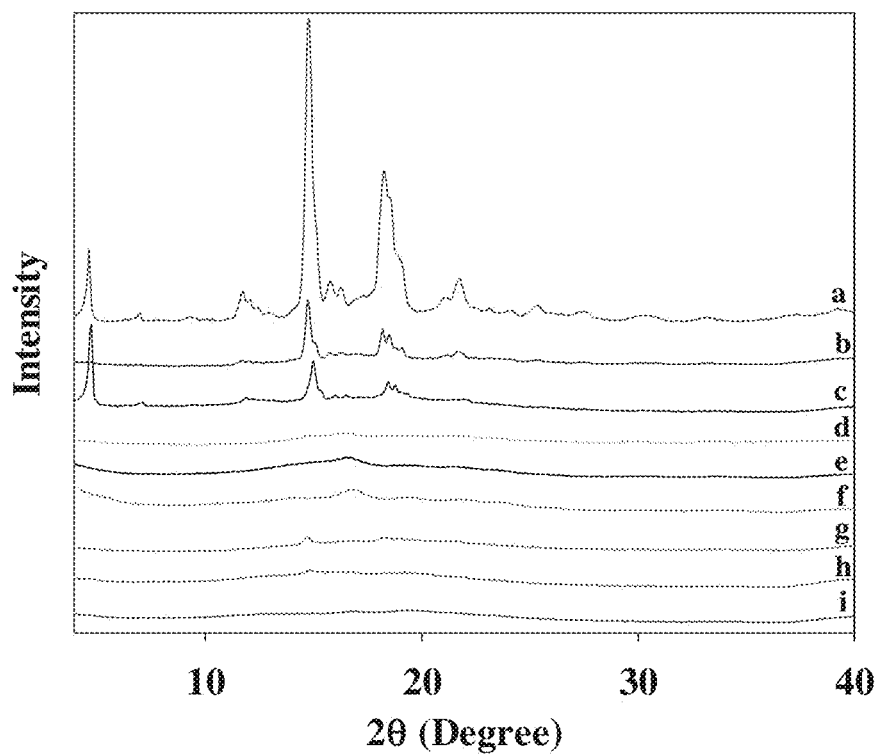
FIG. 18 depicts XRD patterns of (line "a") crude phytosterols, (line "b") physical mixture of crude phytosterols with empty CSA, (line "c") physical mixture of crude phytosterols with empty WSA, (line "d") PS-CSA-P, (line "e") PS-CSA-M, (line "f") empty CSA, (line "g") PS-WSA-P, (line "h") PS-WSA-M, and (line "i") empty WSA.

Crystallinity. XRD patterns of crude phytosterols, physical mixtures of crude phytosterol and empty aerogels, phytosterol impregnated CSAs and WSAs, and empty CSA and WSA revealed strong diffraction peaks at $2\theta=4.60$, 11.7°, 14.7°, 18.2°, and 21.8° (FIG. 18, line "a"). Empty WSA revealed one broad peak as a result of complete gelatinization (FIG. 18, line "i"). However, empty CSA had four broad small peaks at $2\theta=15.00$, 16.8°, 19.4°, and 21.7° (FIG. 18, line "f"). The XRD pattern of the physical mixture of crude phytosterols with WSA-P (126 mg phytosterols/g WSA) had comparable characteristic peaks compared to that of crude phytosterols (FIG. 18, line "c"). Similarly, the physical mixture of crude phytosterols with CSA-P at the same impregnation capacity (195 mg phytosterols/g CSA) showed similar characteristic peaks with crude phytosterols (FIG. 18, line "b"). Those peaks were not observed after impregnation into the aerogels (PS-CSA-P; FIG. 3*d*, PS-CSA-M; FIG. 18, line "e", PS-WSA-M; FIG. 18, line "h"). Reducing the crystallinity of phytosterols by using $SC-CO_2$ impregnation into the nanoporous starch aerogels can improve the water solubility/solubilization of phytosterols due to the increase in the lattice free energy. However, PS-WSA-P showed a small peak at $2\theta=14.70$, which may lead to lower bioaccessibility compared to impregnation into the monolithic shape (FIG. 18, line "g").

Simulated Digestion

Figure 19:
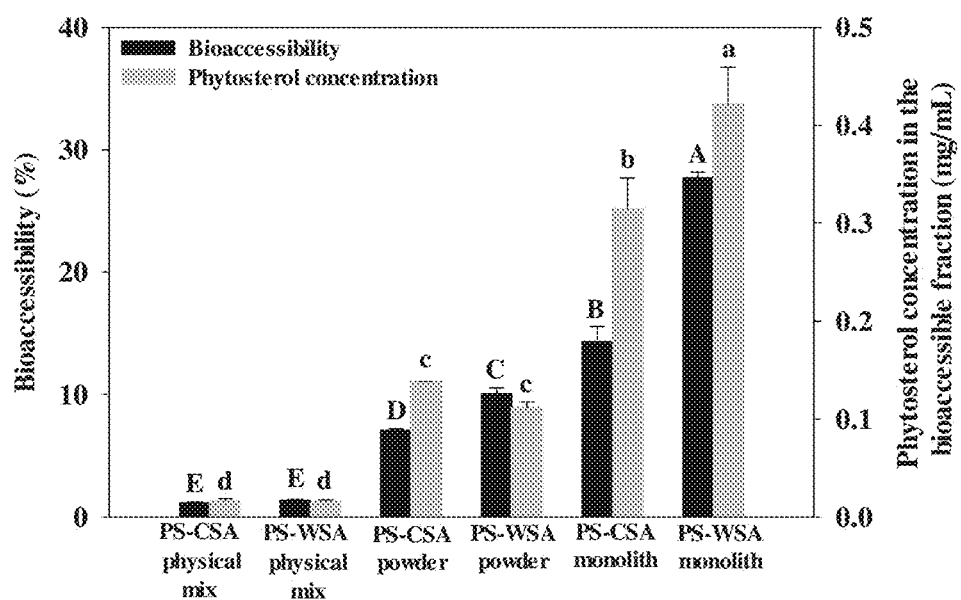
FIG. 19 depicts bioaccessibility and concentration of phytosterols in the bioaccessible fraction after simulated digestion. Different capital letters represent significant differences among the bioaccessibility values of phytosterols ($p<0.05$) and different lowercase letters represent statistical significance in phytosterol concentration in the bioaccessible fraction of the samples ($p<0.05$).

As described in this Example, phytosterol-impregnated starch aerogels underwent a sequential oral, gastric and intestinal digestion to study the hydrolysis of the aerogels and the release of impregnated phytosterols in digestion medium. FIG. 19 depicts the bioaccessibility and the concentration of phytosterols in the bioaccessible fraction after simulated digestion. The bioaccessible fraction was the aqueous phase obtained after centrifugation, referred to herein as the micellar phase. Physical mixtures of the crude phytosterols with WSA or CSA had bioaccessibilities of 1.4 and 1.2%, respectively (FIG. 19). The highest bioaccessibility of phytosterols was achieved with PS-WSA-M as 27.7%, whereas it was 14.3% for PS-CSA-M (FIG. 19). Furthermore, impregnation into powdered aerogels (PS-WSA-P and PS-CSA-P) resulted in significantly lower bioaccessibilities ($p<0.05$) compared to the impregnation into monolithic forms. PS-WSA-P and PS-CSA-P had a plate-like phytosterol crystals as seen in SEM images (FIGS. 17G & 17H). XRD data (FIG. 18, line "g") showed some degree of crystallinity of the phytosterols in PS-WSA-P. Consequently, larger size phytosterols with some crystallinity resulted in lower dissolution in digestive fluids and in turn lower bioaccessibility. Both impregnated phytosterols, in powder and monolith aerogels, exhibited significantly higher bioaccessibility than crude phytosterols ($p<0.05$). The bioaccessibility of phytosterols was improved by 20 fold with $SC-CO_2$ impregnation into WSA-M.

The concentration of phytosterols in the bioaccessible fraction after simulated digestion showed similar bioaccessibility pattern (FIG. 19). The highest phytosterol concentration in the bioaccessible fraction (0.422 mg/mL) was obtained with PS-WSA-M. Crude phytosterol concentrations were 0.015 and 0.017 mg/mL in the WSA and CSA physical mixtures, respectively, which were significantly lower than the impregnated phytosterol concentrations in the bioaccessible fraction ($p<0.05$). These results suggest good agreement between in vitro and in vivo experiments.

Figure 20:
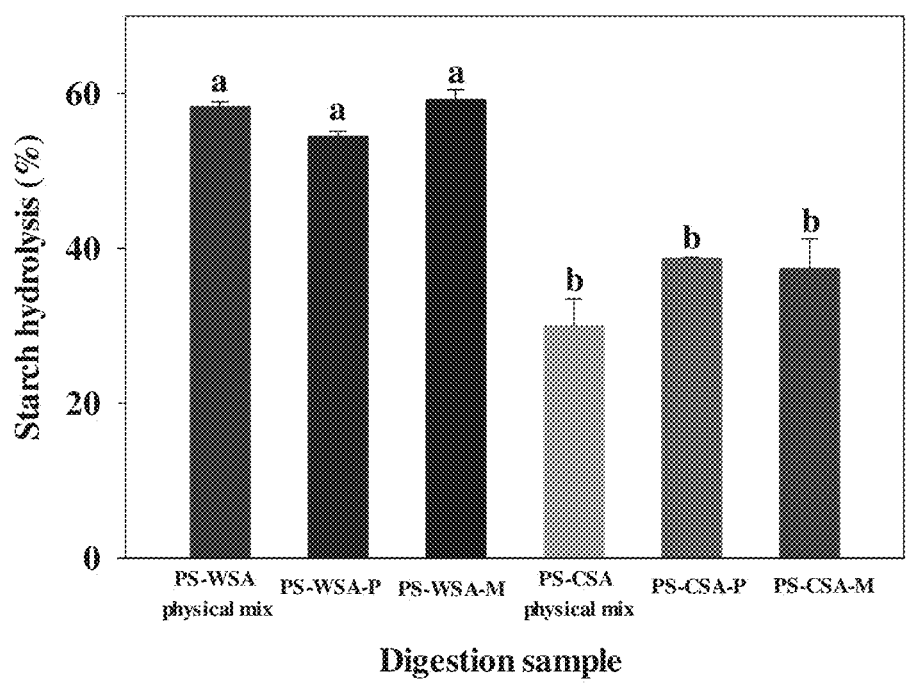
FIG. 20 depicts hydrolysis of the starch aerogels after simulated digestion.

Although, in the present study, the impregnation capacity was improved from 126 mg phytosterol/g WSA to 195 mg phytosterol/g CSA by impregnation into CSA-M (FIG. 16), phytosterols in CSA were less bioaccessible compared to the phytosterols in WSA, possibly due to lower starch hydrolysis during simulated digestion (FIG. 20). Notably, hydrolysis of WSA was significantly higher than that of CSA at all conditions ($p<0.05$). Nonetheless, starch hydrolysis (54.5-59.2%) did not differ among WSA samples indicating there was no effect of the impregnation process on aerogel hydrolysis. On the other hand, CSA hydrolysis was lower and ranged between 30.0-38.6%.

As presented herein, low-crystallinity phytosterol nanoparticles (70 nm) where prepared by a method using $SC-CO_2$ impregnation of phytosterols into nanoporous starch aerogels. Both WSA (surface area of 62 $m^2/g$, pore size of 19 nm and density of 0.11 $g/cm^3$) and CSA (surface area of 221 $m^2/g$, pore size of 7 nm and density of 0.16 $g/cm^3$) decreased the size and crystallinity of phytosterols. The highest impregnation capacity (195 mg phytosterols/g CSA) was achieved by $SC-CO_2$ impregnation of phytosterols into CSA-M. Although the impregnation capacity did not change significantly with the shape of the aerogels, monolith or powder, the morphology of phytosterol crystals was affected as larger plate-like crystals formed following impregnation into powdered aerogels. Phytosterol crystallinity was decreased by $SC-CO_2$ impregnation into aerogels. Phytosterol bioaccessibility was significantly improved from 1.4% to 27.7% with PS-WSA-M. The results provide a nanomanufacturing method that produces dry phytosterol nanoparticle formulations without the use of any emulsifiers or toxic organic solvents, which can be used in food preparations, for example.

In summary, nanoporous starch aerogels from wheat starch were prepared and impregnated with phytosterols using $SC-CO_2$. The nanoporous starch aerogels had an average pore size of 20 nm, and the surface are of one gram of the starch aerogel was approximately 60 $m^2$. The phytosterol was dissolved in the $SC-CO_2$ at 45 MPa and 70° C., and then the pores of the starch aerogel was filled with the phytosterol containing $SC-CO_2$ by a simple diffusion in the same vessel. Then, the temperature of the vessel was decreased to room temperature by natural cooling. The solubility of the phytosterols in the $SC-CO_2$ decreased to zero upon temperature decrease, because the temperature was decreased below the supercritical temperature of the $CO_2$. The phytosterol dissolved in the $SC-CO_2$ precipitated in the nanopores of the starch aerogel due to decrease in their solubility in the $SC-CO_2$. The nanopores of the starch aerogel acted as a mold; prevented formation of big phytosterol crystals and formed phytosterol nanoparticles in the starch aerogel.

This process decreased the size and crystallinity of the phytosterols. Preliminary results showed that the process can form both individual phytosterol nanoparticles and film-like crystals that have nanosize thickness and bigger surface area compared to original larger phytosterol crystals. Impregnating crystalline phytosterol into nanoporous starch aerogels decreased the crystallinity of the phytosterol and changed the crystal morphology, and therefore, improved the water solubility of the phytosterol. Preliminary findings demonstrated that the crystallinity of the phytosterols decreased significantly and therefore their solubility in the water and simulated gastrointestinal fluids increased significantly. Please see Appendix 1, Appendix 2 and Appendix 3 for the technical details such as for the formation and characteristics of the nanoporous starch aerogels, impregnation of the nanoporous starch aerogels with phytosterols, testing the solubility of the phytosterols impregnated in the nanoporous starch aerogels in water and simulated gastrointestinal fluids.

What is claimed is:

1. A nanoporous starch aerogel impregnated with a phytosterol, wherein the phytosterol has reduced crystallinity as compared to crude phytosterol.

2. The aerogel as set forth in claim 1 wherein the nanoporous starch aerogel is a wheat starch aerogel.

3. The aerogel as set forth in claim 1 wherein the phytosterol is selected from the group consisting of β-sitosterol, campesterol, stigmasterol, and combinations thereof.

4. A nanoporous starch aerogel impregnated with a phytosterol, wherein the phytosterol has increased water solubility as compared to crude phytosterol.

5. The aerogel as set forth in claim 4 wherein the phytosterol is selected from the group consisting of β-sitosterol, campesterol, stigmasterol, and combinations thereof.

* * * * *